(12) United States Patent
Kanzius

(10) Patent No.: US 7,510,555 B2
(45) Date of Patent: Mar. 31, 2009

(54) ENHANCED SYSTEMS AND METHODS FOR RF-INDUCED HYPERTHERMIA

(75) Inventor: John Kanzius, Erie, PA (US)

(73) Assignee: Therm Med, LLC, Erie, PA (US)

( * ) Notice: Subject to any disclaimer, the term of this patent is extended or adjusted under 35 U.S.C. 154(b) by 267 days.

(21) Appl. No.: 11/050,422

(22) Filed: Feb. 3, 2005

(65) Prior Publication Data

US 2006/0190063 A1 Aug. 24, 2006

Related U.S. Application Data

(63) Continuation-in-part of application No. 10/969,477, filed on Oct. 20, 2004.

(60) Provisional application No. 60/569,348, filed on May 7, 2004.

(51) Int. Cl.
*A61B 18/18* (2006.01)

(52) U.S. Cl. .................. 606/33; 424/9.34; 128/898

(58) Field of Classification Search .......... 128/898; 424/9.1–9.4; 606/27–52
See application file for complete search history.

(56) References Cited

U.S. PATENT DOCUMENTS

| | | |
|---|---|---|
| 2,223,447 A | 12/1940 | Hathaway |
| 2,249,935 A | 7/1941 | Birtcher |
| 2,407,690 A | 9/1946 | Southworth |
| 2,543,248 A | 2/1951 | Ledeboer et al. |
| 2,556,556 A | 6/1951 | Schmitt et al. |
| 2,635,606 A | 4/1953 | Hanway |
| 2,656,839 A | 10/1953 | Howard |
| 2,698,622 A | 1/1955 | Martens |
| 2,838,672 A | 6/1958 | Paust |
| 3,077,195 A | 2/1963 | Folsche |
| 3,181,535 A | 5/1965 | Milinowski |
| 3,245,408 A | 4/1966 | Gonser |
| 3,509,465 A | 4/1970 | Andre et al. |

(Continued)

FOREIGN PATENT DOCUMENTS

EP 0 325 456 7/1989

(Continued)

OTHER PUBLICATIONS

"Sparks of Genius: Faced with cancer, a radio executive had an idea. Could his late-night tinkering lead to a cure?" by Peter Panepento, RD, May 2006, pp. 132-138.

(Continued)

*Primary Examiner*—Henry M Johnson, III
(74) *Attorney, Agent, or Firm*—Calfee, Halter & Griswold LLP

(57) ABSTRACT

A method of inducing hyperthermia in at least a portion of a target area—e.g., a tumor or a portion of a tumor or targeted cancerous cells—is provided. Targeted RF absorption enhancers, e.g., antibodies bound to RF absorbing particles, are introduced into a patient. These targeted RF absorption enhancers will target certain cells in the target areas and enhance the effect of a hyperthermia generating RF signal directed toward the target area. The targeted RF absorption enhancers may, in a manner of speaking, add one or more RF absorption frequencies to cells in the target area, which will permit a hyperthermia generating RF signal at that frequency or frequencies to heat the targeted cells.

73 Claims, 24 Drawing Sheets

U.S. PATENT DOCUMENTS

| | | |
|---|---|---|
| 3,543,762 A | 12/1970 | Kendall |
| 3,747,013 A | 7/1973 | Mettler |
| 3,800,802 A | 4/1974 | Berry et al. |
| 3,991,770 A | 11/1976 | LeVeen |
| 4,032,860 A | 6/1977 | LeVeen |
| 4,095,602 A | 6/1978 | Leveen |
| 4,106,488 A | 8/1978 | Gordon |
| 4,119,102 A | 10/1978 | LeVeen |
| 4,121,592 A | 10/1978 | Whalley |
| 4,140,130 A | 2/1979 | Storm, III |
| 4,154,246 A | 5/1979 | LeVeen |
| 4,210,152 A | 7/1980 | Berry |
| 4,230,129 A | 10/1980 | LeVeen |
| 4,237,898 A | 12/1980 | Whalley |
| 4,282,887 A | 8/1981 | Sterzer |
| 4,285,346 A | 8/1981 | Armitage |
| 4,303,636 A | 12/1981 | Gordon |
| 4,325,361 A | 4/1982 | Harrison |
| 4,356,458 A | 10/1982 | Armitage |
| 4,392,040 A | 7/1983 | Rand et al. |
| 4,402,309 A | 9/1983 | Harrison |
| 4,412,540 A | 11/1983 | Bentall |
| 4,429,698 A | 2/1984 | Bentall |
| 4,471,787 A | 9/1984 | Bentall |
| RE32,057 E | 12/1985 | LeVeen |
| RE32,066 E | 1/1986 | Leveen |
| 4,587,978 A | 5/1986 | Suyama et al. |
| 4,595,008 A | 6/1986 | Guibert |
| 4,667,658 A | 5/1987 | Guibert |
| 4,667,677 A | 5/1987 | De Mino et al. |
| 4,674,481 A | 6/1987 | Boddie et al. |
| 4,679,561 A | 7/1987 | Doss |
| 4,700,179 A | 10/1987 | Fancher |
| 4,785,829 A | 11/1988 | Convert et al. |
| 4,800,899 A | 1/1989 | Elliott |
| 4,823,811 A | 4/1989 | Harrison |
| 4,823,813 A | 4/1989 | Harrison |
| 4,878,493 A | 11/1989 | Pasternak et al. |
| 4,977,380 A | 12/1990 | Martin et al. |
| 4,983,159 A | 1/1991 | Rand |
| 5,003,991 A | 4/1991 | Takayama et al. |
| 5,010,897 A | 4/1991 | Leveen |
| 5,057,095 A | 10/1991 | Fabian |
| 5,099,756 A | 3/1992 | Franconi et al. |
| 5,099,840 A | 3/1992 | Goble et al. |
| 5,128,147 A * | 7/1992 | Leveen et al. ............... 424/497 |
| 5,186,181 A | 2/1993 | Franconi et al. |
| 5,249,575 A | 10/1993 | De Mino et al. |
| 5,260,050 A | 11/1993 | Ranney |
| 5,371,342 A | 12/1994 | Saitoh |
| 5,386,837 A * | 2/1995 | Sterzer ...................... 128/898 |
| 5,411,730 A * | 5/1995 | Kirpotin et al. .......... 424/9.322 |
| 5,478,303 A | 12/1995 | Foley-Nolan et al. |
| 5,676,695 A | 10/1997 | De Mino et al. |
| 5,827,276 A | 10/1998 | LeVeen et al. |
| 5,855,576 A | 1/1999 | LeVeen et al. |
| 5,868,740 A | 2/1999 | LeVeen et al. |
| 5,922,013 A | 7/1999 | Fallik |
| 5,935,390 A | 8/1999 | Felix et al. |
| 5,983,141 A | 11/1999 | Sluijter et al. |
| 6,139,819 A | 10/2000 | Unger et al. |
| 6,165,440 A | 12/2000 | Esenaliev |
| 6,212,432 B1 | 4/2001 | Matsuura |
| 6,240,319 B1 | 5/2001 | Rogers |
| 6,424,820 B1 | 7/2002 | Burdick et al. |
| 6,424,864 B1 | 7/2002 | Matsuura |
| 6,425,877 B1 * | 7/2002 | Edwards ..................... 604/21 |
| 6,454,765 B1 | 9/2002 | Leveen et al. |
| 6,468,273 B1 | 10/2002 | Leveen et al. |
| 6,470,217 B1 | 10/2002 | Fenn et al. |
| 6,512,955 B1 | 1/2003 | McEnany et al. |
| 6,530,944 B2 | 3/2003 | West et al. |
| 6,575,967 B1 | 6/2003 | Leveen et al. |
| 6,622,731 B2 * | 9/2003 | Daniel et al. ................ 128/898 |
| 6,662,054 B2 | 12/2003 | Kreindel et al. |
| 6,864,755 B2 | 3/2005 | Moore |
| 6,997,863 B2 | 2/2006 | Handy et al. |
| 7,005,935 B2 | 2/2006 | Moore |
| 7,022,105 B1 * | 4/2006 | Edwards ................ 604/103.01 |
| 7,074,175 B2 | 7/2006 | Handy et al. |
| 7,108,696 B2 * | 9/2006 | Daniel et al. ................... 606/41 |
| 7,163,664 B2 | 1/2007 | Paskalov et al. |
| 7,291,314 B2 | 11/2007 | Paskalov et al. |
| 2002/0026224 A1 | 2/2002 | Thompson et al. |
| 2002/0045920 A1 | 4/2002 | Thompson |
| 2003/0195410 A1 | 10/2003 | Winter |
| 2004/0044385 A1 * | 3/2004 | Fenn et al. ................... 607/100 |
| 2004/0050682 A1 | 3/2004 | Paskalov et al. |
| 2004/0059328 A1 * | 3/2004 | Daniel et al. ................... 606/41 |
| 2004/0069618 A1 | 4/2004 | Paskalov et al. |
| 2004/0141876 A1 | 7/2004 | Paskalov et al. |
| 2004/0199070 A1 * | 10/2004 | Krockel ...................... 600/412 |
| 2004/0210282 A1 | 10/2004 | Flock et al. |
| 2004/0229295 A1 | 11/2004 | Marchitto et al. |
| 2004/0253181 A1 | 12/2004 | Port et al. |
| 2005/0056596 A1 | 3/2005 | Paskalov et al. |
| 2005/0090732 A1 * | 4/2005 | Ivkov et al. ................. 600/411 |
| 2005/0118102 A1 * | 6/2005 | Xiang et al. ............... 424/9.34 |
| 2005/0251233 A1 | 11/2005 | Kanzius |
| 2005/0251234 A1 | 11/2005 | Kanzius et al. |
| 2005/0273143 A1 | 12/2005 | Kanzius et al. |
| 2006/0047328 A1 | 3/2006 | Murphy |
| 2006/0206180 A1 | 9/2006 | Alcidi |

FOREIGN PATENT DOCUMENTS

| | | |
|---|---|---|
| EP | 0 713 715 | 5/1996 |
| WO | WO 90/01353 | 2/1990 |
| WO | 91/07132 | 5/1991 |
| WO | 2005/110261 | 11/2005 |
| WO | 2005/110544 | 11/2005 |
| WO | WO 2005/118065 | 12/2005 |
| WO | WO 2005/120639 | 12/2005 |
| WO | WO 2007/027614 | 3/2007 |

OTHER PUBLICATIONS

"Modulated Chemical Doping of Individual Carbon Nanotubes" by Zhou, et al., Science, Nov. 24, 2000, vol. 290, No. 5496, pp. 1552-1555.

"Houston cancer center starts testing radio-wave theory" Erie Times-News, Nov. 25, 2005.

"Cancer Therapy to Take Next Step" by Peter Panepento, Erie Times-News, May 23, 2006.

International Search Report from PCT/US06/033552, dated Jan. 30, 2007.

"Synthesis and evaluation of colloidal magnetic iron oxides for the site-specific radiofrequency-induced hyperthermia of cancer" by Chan, et al., Journal of Magnetism and Magnetic Materials 122 (1993) 374-378.

"Radiofrequency Capacitive Hyperthermia for Deep-Seated Tumors" by Hiraoka, et al., Cancer, 60:121-127, 1987.

"Cancer Therapy Takes Next Step: Millcreek inventor's method shown effective against malignant cells" by Panepento, Erie Times-News, Mar. 22, 2006.

"Functionalization density dependence of single-walled carbon nanotubes cytotoxicity in vitro" by Sayes, et al., Toxicology Letter 161 (2006) 135-142.

"Individually Suspended Single-Walled Carbon Nanotubes in Various Surfactants" by Moore, et al., Nano Letters, 2003, vol. 3, No. 10, 1379-1382.

Armitage, D.W., et al., Radiofrequency-induced hyperthermia: computer simulation of specific absorption rate distributions using realistic anatomical models, stacks.iop.org/0013-9155/28/31, Jan. 1983 (Abstract).

Brusentsov, N.A., et al., Hyperthermia of Tumors at 0.88 MHz, Russian Cancer Research RAMS, Radiotechnical Research Institute, Russia, Moscow, Sep. 1999 (Abstract).

Buscarini, L., et al., Laparoscopic ablation of liver adenoma by radiofrequency electrocauthery, Gastrointestinal Endoscopy, vol. 41, No. 1, 1995, pp. 68-70.

Chen, A., et al., Cross-Linking of Cell Surface Receptors Enhances Cooperativity of Molecular Adhesion, Biophysical Journal, vol. 78, Jun. 2000, pp. 2814-2820.

Chen, R.J., et al., Noncovalent functionalization of carbon nanotubes for highly specific electronic biosensors, PNAS, Apr. 29, 2003, vol. 100, No. 9, pp. 4984-4989.

Cohn, J.G., Selected Properties of Gold, http://www.gold.org/discover/sci_indu/properties/pdf/Propertysummary.pdf?PHPSESSID=c04b8cd98e98005c4e1186191bd8db, accessed Nov. 12, 2004.

Curley, S., et al., Direct Intratumoral Injection of a Novel Collagen Matrix Gel and Cisplatin Effectively Controls Experimental Liver Tumors, Cancer Research, Therapy and Control, 1995, vol. 4, pp. 247-254.

Curley, S., et al., Early and Late Complications After Radiofrequency Ablation of Malignant Liver Tumors in 608 Patients, Annals of Surgery, vol. 239, No. 4, 2004, pp. 450-458.

Curley, S., et al., Radiofrequency Ablation of Epatocellular Cancer in 110 Patients with Cirrhosis, Annals of Surgery, vol. 232, No. 3, Apr. 6-8, 2000, pp. 381-391.

Curley, S., et al., Radiofrequency Ablation of Unresectable Primary and Metastatic Hepatic Malignancies, Annals of Surgery, vol. 230, No. 1, Jul. 1999, pp. 1-8.

Denardo, G.L., Radiometals as Payloads for Radioimmunotherapy for Lymphoma, Clinical Lymphoma, vol. 5, Suppl. 1, Oct. 2004, pp. S5-S10.

Francesco, I., et al., Radiofrequency Ablation in Patients with Primary Breast Carcinoma, Cancer, vol. 92, No. 8, Oct. 15, 2001, pp. 2036-2044.

Freitas, Jr., R.A., 15.3.5.5 Alumina and Sapphire Particles, Nanomedicine, vol. IIA: Biocompatibility, 2003.

Hiraoka, A.M., et al, Multi-institutional studies on hyperthermia using an 8-MHz radiofrequency capacitive heating device (Thermotron RF-8) in combination with radiation for cancer therapy, Cancer, vol. 58, No. 8, Oct. 15, 1986, pp. 1589-1595 (Abstract).

Hirsch, L.R., et al., Nanoshell-mediated near-infrared thermal therapy of tumors under magnetic resonance guidance, PNAS, vol. 100, No. 23, Nov. 11, 2003, pp. 13549-13554.

Huard, Benjamin, Some properties of carbon nanotubes and fullerenes, Research Training Course, MIP second year, Materials Science Div.; Lawrence Berkeley National Laboratory, Berkeley, California, USA; Jan. 2002-Jul. 2002, pp. 1-42.

Johnson, S., et al., Biocompatibility studies on plasm polymerized interface materials encompassing both hydrophobi and hydrophilic surfaces, Journal of Biomedical Materials Research, vol. 26, Issue 7, Sep. 13, 2004, pp. 915-935 (Abstract).

Kam, N.W.S., et al, Carbon Nanotubules as Intracellular Protein Transporters: Generality and Biological Functionality, J. Am. Chem. Soc., 2005, 127, pp. 6021-6026.

Kam, N.W.S., et al., Carbon nanotubules as multifunctional biological transporters and near-infrared agents for selective cancer cell destruction, PNAS, vol. 102, No. 33, Aug. 16, 2005, pp. 11600-11605.

Katakura, Jun-Ichi, Present Status of Jendl Project, WPEC 2004, May 25-28, 2004 presentation.

Kirchner, P.T., et al., Survey of Radionuclide Use and Needs by Recipients of DOE-BER Grans Apr.-May 2002, Office of Biological and Environmental Research, Office of Science, Department of Energy presentation, accessed on Nov. 12, 2004.

Kuznetsov, A.A., et al., "Smart" Mediators for Self-Controlled Inductive Heating, European Cells and Materials, vol. 3, Suppl. 2, 2002, pp. 75-77.

Leveen, H.H., et al., Tumor Eradication by Radiofrequency Therapy Response in 21 Patients, JAMA, vol. 235, No. 20, May 17, 1976, pp. 2198-2200.

Larina, I.V., et al., Enhancement of Drug Delivery in Tumors by Using Interaction of Nanoparticles with Ultrasound Radiation, Technology in Cancer & Treatment, vol. 4, No. 2, Apr. 2005, pp. 217-226.

Odenbach, S., Dr., Ferrofluids: magnetically controllable liquids, ZARM, University of Bremen, Am Gallturm, 28359 Bremen, Germany, Mar. 2002 (Abstract).

O'Neal, D. Patrick, Photo-thermal tumor ablation in mice using near infrared-absorbing nanoparticles, Cancer Letters, vol. 209, 2004, pp. 171-176.

Panepento, Peter, Cancer test expand, Erie Times News, Jun. 2005, goerie.com.

Panepento, Peter, Cancer treatment heralded; Millcreek man's radio waves procedure leaves expert optimistic, timesnews.com, Jul. 2004.

Panepento, Peter, Intial test backs Kanzius theory, Erie Times News, Aug. 9, 2005, goerie.com.

Panepento, Peter, Specter backs Kanzius effort, Erie Times, Aug. 25, 2004.

Pankhurst, Q.A., et al., Applications of magnetic nanoparticles in biomedicine, J. Phys. D: Appl. Phys. 36 (2003) R167-R181.

Pitsillides, C.M., et al., Selective Cell Targeting with Light-Absorbing Microparticles and Nanoparticles, Biophysical Journal, vol. 84, Jun. 2003, pp. 4023-4032.

Rossi, S., et al., Thermal Lesions Induced by 480 KHz Localized Current Field in Guinea Pig and Pig Liver, Tumori, vol. 76, 1990, pp. 54-57.

Sadana, A.K., et al., Functionalization and Extraction of Large Fullerenes and Carbon-Coated Metal Formed during the Synthesis of SingleWall Carbon Nanotubes by Laser Oven, Direct Current Arc, and High-Pressure Carbon monoxide Production Methods, J. Phys. Chem. B 2005, vol. 109, pp. 4416-2218.

Sayes, C.M., et al., Functionalization density dependence of singlewalled carbon nanotubes cytotoxicity in vitro, Toxicology Letters, vol. 161, (2006) pp. 135-142.

Senger, R.T., et al., Chiral Single-Wall Gold Nanotubes, Physical Review Letters, vol. 93, No. 19, Nov. 5, 2004, pp. 196808:1-4.

Shinkai, M., et al., Effect of Functional Magnetic particles on Radiofrequency Capacitive Heating: An in vivo study, Jpn J. Cancer Res., vol. 93, No. 1, Jan. 2002, pp. 103-108.

Smalley, M.J., et al., Wnt signalling mammalian development and cancer, Cancer Metastasis Rev., vol. 18, No. 2, 1999, pp. 215-230 (Abstract).

Templeton, David, Funding sought for radio wave cancer therapy, http://www.post-gazette.com/pg/04243/369981.stm, Aug. 30, 2004.

Templeton, David, Nobel Prize winner to join cancer research team, Pittsburgh Post-Gazette, Jul. 22, 2005, www.post-gazette.com.

Templeton, David, Novel cancer treatment demonstrated at UPMC lab, Pittsburgh Post-Gazette, Aug. 6, 2005, www.post-gazette.com.

Templeton, David, UPMC set to test cancer treatment; inventor fashions radio-wave device as possible cure; http://postgazette.com/pg/05051/459069.stm, Feb. 20, 2005.

Uo, M., et al., Quantitative analysis of biologic specimens by X-ray scanning analytic microscopy, Journal of Biomedical Materials Research Part B: Applied Biomaterials, vol. 70B, Issue 1, pp. 146-151, Mar. 8, 2004 (Abstract).

Van Der Zee, J., Heating the patient: a promising approach?, Annals of Oncology 13, pp. 1173-1184, Aug. 8, 2002.

Wada, S., et al., New local hyperthermia using dextran magetite complex (DM) for oral cavity: experimental study in normal hamster tongue, May 2001 (Abstract).

Walivaara, B., et al., Antisera binding onto metals immersed in human plasma in vitro, Journal of Biomedical Materials Research, vol. 26, Iss 9, Sep. 13, 2004 pp. 1205-1216 (Abstract).

The basic tehniko-operational parameters new domestic UVCH-gipertermicheskogo complex EKSTRATERM. Local UVCH-gipertermija, spent with the use of complex EKSTRATERM, in treatment of malignant tumours of various localizations, accessed on Apr. 5, 2004, www.extratherm.ru.

The basic tehniko-operational parameters new domestic YB4-rhneptepmh4eckoto complex EKCTPATEPM. Local YB4-rhneptepmhr, spent with the use of complex EKCTPATEPM, in treatment of malignant tumours of various locations, accessed on Apr. 5, 2004, www.extratherm.ru (different translation setting than Ref. 87).

Buckyballs and Buckytubes, http://buckyballs2buckytubes.homestead.com/index2~ns4.html, accessed Aug. 18, 2005.
Chemistry of Nanoscale Materials; Synthesis, Properties and Applications presentation, Dec. 15, 2004.
Workshop of Fullerenes Set 95, Buckminsterfullerene C60, Sussex Fullerene Grp, Univ of Sussex; http://www.creative-science.org.uk/workshops/c60/workshop.html, accessed Aug. 18, 2005.
Medical Radioisotoper & Applications, http://web.archive.org/web/20060210104141/http://www.radiochemistry.org/nuclearmedicine/frames/medical_radioisotopes/me..., acc Dec. 15, 2004.
Multitalented Nanoparticles Pop Genes into Cells, http:/www.betterhumans.com/News/4136/Default.aspx, Dec. 27, 2004.
Nobel winner boosts Kanzius; Acclaimed chemist excited by Erie man's cancer-fighting strategy, Erie Times, goerie.com, Jul. 17, 2005.
Nuclide information, http:/www.ndc.tokai.jaeri.go.jp/cgi-bin/nuclinfo2003?79,197, accessed Apr. 12, 2004.
Periodic Table of the Elements: Thermal Conductivity, http://web.mit.edu/3.091/222/pt/pert14.html, accessed Jan. 25, 2005.
Periodic table: Gold, http://www.chemicalelements.com/elements/au.html, accessed Nov. 12, 2004.
Properties of Gold, http:/www.gold.org/discover/sci_indu/properties/, accessed Nov. 12, 2004.
The Proteasome, http://users.rcn.com/jkimball.ma.ultranet/BiologyPages/P/Proteasome.html, May 16, 2004.
Rituxan (Rituximab), http://web.archive.org/20040404102708/http://tirgan.com/rituxan.htm, accessed on Apr. 5, 2004.
Rituxan (Rituximab), http://www.gene.com/gene/products/information/oncology/rituxan/index.jsp?hl=en&lr=&q..., accessed on Apr. 5, 2004.
Rituxan (Rituximab) Answers to questions you may have about your treatment with Rituxan, http://web.archive.org/20040404081338/www.rituxan.com/rituxan/patient/questions, accessed on Apr. 5, 2004.
Rituxan (Rituximab) A breakthrough treatment, http://web.archive.org/web/20040404092359/http://www.rituxan.com/rituxan/patient/why/..., accessed on Apr. 5, 2004.
"Towards breast cancer treatment by magnetic heating" by Hilger, et al., Journal of Magnetism and Magnetic Materials, 293 (2005) 314-319.
Abstract—"Carbon nanotubes: properties and application" by Popov, et al., Materials Science and Engineering: R: Reports, vol. 43, Issue 3, Jan. 15, 2004, p. 61-102, available online Dec. 13, 2003.
"Specific Absorption Rate and Temperature Elevation in a Subject Exposed in the Far-Field of Radio-Frequency Sources Operating in the 10-900-MHz Range" by Bernardi, et al., IEEE Transactions on Biomedical Engineering, vol. 50, No. 3, Mar. 2003, pp. 295-304.
"Extraordinary Mobility in Semiconducting Carbon Nanotubes" by Durkop, et al., Nano Letters, 2004, vol. 4, No. 1, 35-39.
"Singe-Walled Carbon Nanotube Electronics" by McEuen, et al., IEEE Transactions on Nanotechnology, 2002.
"Part 18—Industrial, Scientific, and Medical Equipment", Code of Federal Regulations, 47, Parts 0 to 19, Revised as of Oct. 1, 2006, pp. 938-945, U.S. Government Printing Office, Washington, D.C.
Chen et al., "Noncovalent functionalization of carbon nanotubes for highly specific electronic biosensors", Jun. 25, 2005, PNAS, Apr. 29, 2003, vol. 100, No. 9, pp. 4984-4989.
Bachilo et al., "Structure-Assigned Optical Spectra of Single-Walled Carbon Nanotubes", Dec. 20, 2002, Science, vol. 298, pp. 2361-2366.
Bachtold et al., "Scanned probe Microscopy of Electronic Transport in Carbon Nanotubes", Jun. 26, 2000, Physical Review Letters, vol. 84, No. 26, pp. 6082-6085.
Baugham et al., "Carbon Nanotubes—the Route Toward Applications", Aug. 2, 2002, Science, vol. 297, pp. 787-792.
Durney et al., "Radiofrequency radiation dosimetry handbook" 1986, USAF School of Aerospace Medicine Press.
Sandler et al., "Ultra-low electrical percolation threshold in carbon-nanotube-epoxy composites", 2003, Polymer, 44, pp. 5893-5899.
Hergt et al., "Maghemite nanoparticles with very high AC-losses for application in RF-magnetic hyperthermia", 2004, J of Magnetism and Magnetic Materials, 270, pp. 345-357.
Iijima, "Helical microtubules of graphitic carbon", Nov. 7, 1991, Letters to Nature, vol. 354, pp. 56-58.
Landau et al., "Electrodynamics of continuous media", 2004, Elsevier, Oxford, pp. 8-19.
Specification sheet for Yaesu transceiver FT-1000MP from Yaesu web site of Apr. 7, 2003.
International Search Report mailed on Aug. 18, 2005, for International Application No. PCT/US2005/016079.
Butler, Lloyd RF Power Amplifiers - Tank Circuits & Output Coupling, Amateur Radio (magazine), May 1988, pp. 1-8.
Office Action mailed Sep. 15, 2008 for U.S. Appl. No. 11/215,825 (the Office already has a copy of the Office Action; in accordance with discussions with Examiner Henry M. Johnson III, no copies need to be submitted; if the Office would like a copy of the Office Action to be submitted, please advise).
Office Action mailed Sep. 16, 2008 for U.S. Appl. No. 11/050,478 (the Office already has a copy of the Office Action; in accordance with discussions with Examiner Henry M. Johnson III, no copies need to be submitted; if the Office would like a copy of the Office Action to be submitted, please advise).
Remarks in Amendment After Final submitted to the U.S. Patent Office on Oct. 13, 2008, in response to the Office Action mailed Sep. 16, 2008 for related U.S. Appl. No. 11/050,478 (the Office already has a copy of this Amendment; in accordance with discussions with Examiner Henry M. Johnson III, no copies need to be submitted; if the Office would like another copy of this Amendment to be submitted, please advise).
Office Action mailed Aug. 19, 2008 for Canadian Application No. 2,562,625, Examiner Saadia Khan.

* cited by examiner

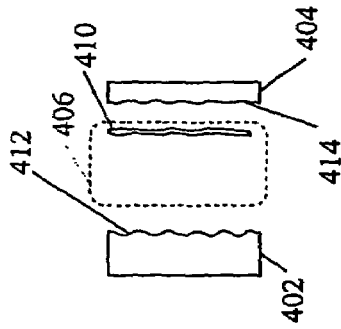
FIG. 4
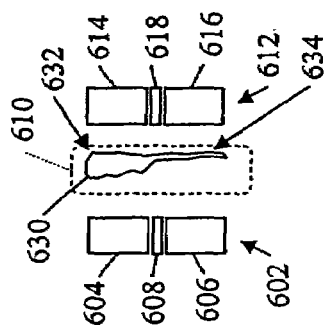
FIG. 3A
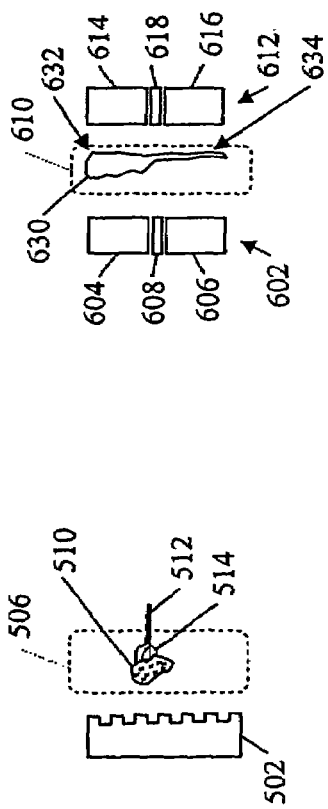
FIG. 6
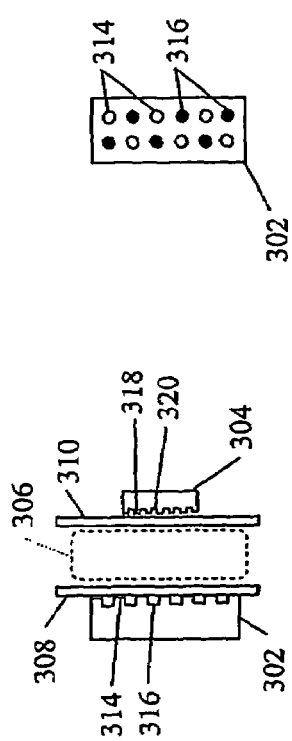
FIG. 3
FIG. 5

ENHANCED SYSTEMS AND METHODS FOR RF-INDUCED HYPERTHERMIA

CROSS REFERENCE TO RELATED APPLICATIONS

This application claims priority to, and the benefits of, provisional application Ser. No.: 60/569,348 filed on May 7, 2004, which is entitled System and Method For RF-Induced Hyperthermia, and which is incorporated herein by reference. This application is also a continuation in part of and claims priority to non-provisional application Ser. No.: 10/969,477 filed on Oct. 20, 2004, which is also entitled System and Method for RF-Induced Hyperthermia, which is currently pending, and which is incorporated herein by reference. This application is also related to U.S. patent application Ser. No. 11/050,478, filed herewith and entitled Systems and Methods for Combined RF-Induced Hyperthermia and Radioimmunotherapy, which is currently pending, and related to U.S. patent application Ser. No. 11/050,481, filed herewith and entitled Systems and Methods for RF-Induced Hyperthermia Using Biological Cells and Nanoparticles as RF Enhancer Carriers, which is currently pending, both of which are incorporated herein by reference.

FIELD OF THE INVENTION

The present invention relates generally to the field of radio frequency (RF) circuits, and more specifically to an RF transmitter and receiver system and method for inducing hyperthermia in a target area.

BACKGROUND OF THE INVENTION

Hyperthermia is characterized by a very high fever, especially when induced artificially for therapeutic purposes. RF electromagnetic energy is electromagnetic energy at any frequency in the radio spectrum from 9000 Hz to 3 THz (3000 GHz). It is known in the art to use contact antennas to direct RF electromagnetic radiation to intentionally induce hyperthermia in human tissue for therapeutic purposes, e.g., destroying diseased cells (e.g., U.S. Pat. No. 4,800,899). There are also several other prior art RF heating devices described in various publications (e.g., the Thermotron RF-8 system, Yamamoto Viniter Co. of Osaka, Japan, and the ЭКСТРАТЕРМ system, Russia, and U.S. Pat. No. 5,099,756; Re. 32,066; and U.S. Pat. No. 4,095,602 to LeVeen).

SUMMARY OF THE INVENTION

In accordance with one exemplary embodiment of the present invention, a method of inducing hyperthermia in at least a portion of a target area—e.g., a tumor or a portion of a tumor or targeted cancerous cells—is provided. In this first exemplary method, targeted RF absorption enhancers, e.g., antibodies bound to RF absorbing particles, are introduced into a patient. These targeted RF absorption enhancers will target certain cells in the target areas and enhance the effect of a hyperthermia generating RF signal directed toward the target area. The targeted RF absorption enhancers may, in a manner of speaking, add one or more artificial RF absorption frequencies to cells in the target area, which will permit a hyperthermia generating RF signal at that frequency or frequencies to heat the targeted cells.

In accordance with another exemplary embodiment of the present invention, another method of inducing hyperthermia in at least a portion of a target area is provided. In this second exemplary method RF absorption enhancers (targeted and/or non-targeted) are introduced into a patient and a multifrequency hyperthermia generating RF signal is directed toward the target area. The multifrequency hyperthermia generating RF signal may be a frequency modulated (FM) signal having parameters selected to correspond to a sample of particles being used as energy absorption enhancer particles in the RF absorption enhancers. For example, the center frequency of an FM hyperthermia generating signal may correspond to a resonant frequency of nominally sized particles used as energy absorption enhancer particles and the modulation of the FM hyperthermia generating signal may correspond to a size tolerance of the particles.

BRIEF DESCRIPTION OF THE DRAWINGS

FIGS. 3, 3A, 4, 5 and 6 are exemplary embodiments of transmission heads and reception heads on either side of a target areas;

DETAILED DESCRIPTION

In the accompanying drawings which are incorporated in and constitute a part of the specification, exemplary embodiments of the invention are illustrated, which, together with a general description of the invention given above, and the detailed description given below, serve to example principles of the invention.

Figure 1:
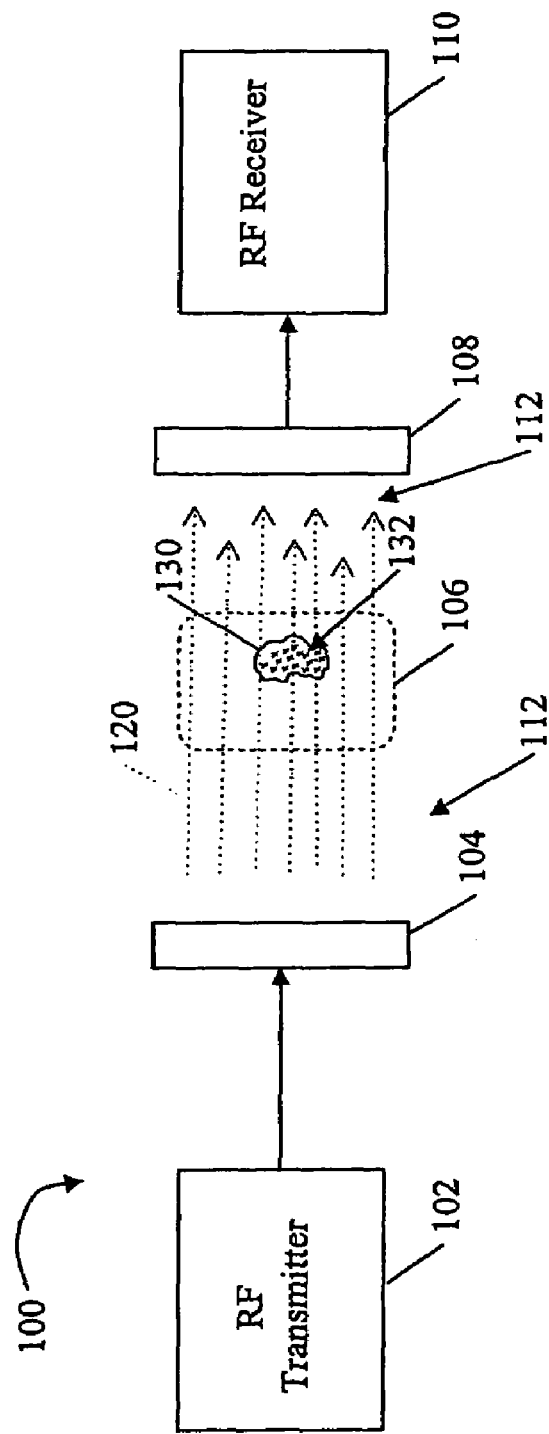
FIG. 1 is an exemplary high-level block diagram of a non-invasive RF system for inducing hyperthermia in a target area.

Referring to the drawings, and initially to FIG. 1, there is shown a first exemplary embodiment of a non-invasive RF system 100 for inducing hyperthermia in a target area 106. System 100 comprises an RF transmitter 102 in circuit communication with a transmission head 104 and an RF receiver 110 in circuit communication with a reception head 108. "Circuit communication" as used herein is used to indicate a communicative relationship between devices. Direct electrical, optical, and electromagnetic connections and indirect electrical, optical, and electromagnetic connections are examples of circuit communication. Two devices are in circuit communication if a signal from one is received by the other, regardless of whether the signal is modified by some other device. For example, two devices separated by one or more of the following—transformers, optoisolators, digital or analog buffers, analog integrators, other electronic circuitry, fiber optic transceivers, or even satellites—are in circuit communication if a signal from one reaches the other, even though the signal is modified by the intermediate device(s). As a final example, two devices not directly connected to each other (e.g. keyboard and memory), but both capable of interfacing with a third device, (e.g., a CPU), are in circuit communication.

In exemplary system 100, the RF transmitter 102 generates an RF signal 120 at a frequency for transmission via the transmission head 104. Optionally, the RF transmitter 102 has controls for adjusting the frequency and/or power of the generated RF signal and/or may have a mode in which an RF signal at a predetermined frequency and power are transmitted via transmission head 104. In addition, optionally, the RF transmitter 102 provides an RF signal with variable amplitudes, pulsed amplitudes, multiple frequencies, etc.

The RF receiver 110 is in circuit communication with the reception head 108. The RF receiver 110 is tuned so that at least a portion of the reception head 108 is resonant at the frequency of the RF signal 120 transmitted via the transmission head 104. As a result, the reception head 108 receives the RF signal 120 that is transmitted via the transmission head 104.

The transmission head 104 and reception head 108 are arranged proximate to and on either side of a general target area 106. General target 106 is general location of the area to be treated. The general target area 106 is any target area or type of cells or group of cells, such as for example, tissue, blood cells, bone marrow cells, etc. The transmission head 104 and reception head 108 are preferably insulated from direct contact with the general target area 106. Preferably, the transmission head 104 and reception head 108 are insulated by means of an air gap 112. Optional means of insulating the transmission head 104 and reception head 108 from the general target area 106 include inserting an insulating layer or material 310 (FIG. 3), such as, for example, Teflon® between the heads 104, 108 and the general target area 106. Other optional means include providing an insulation area on the heads 104, 108, allowing the heads to be put in direct contact with the general target area 106. The transmission head 104 and the reception head 108, described in more detail below, may include one or more plates of electrically conductive material.

The general target area 106 absorbs energy and is warmed as the RF signal 120 travels through the general target area 106. The more energy that is absorbed by an area, the higher the temperature increase in the area. Generally, the general target area 106 includes a specific target area 130. Specific target area 130 includes the tissue or higher concentration of cells, such as, for example, a tumor, that are desired to be treated by inducing hyperthermia. Preferably, the general target area is heated to for example, to between 106° and 107°. Thus, preferably, the specific target area 130 receives higher concentrations of the RF signal 120 then the general target area 106. As a result, the specific target area 130 absorbs more energy, resulting in a higher temperature in the specific target area 130 than in the surrounding general target area 106.

Energy absorption in a target area can be increased by increasing the RF signal 120 strength, which increases the amount of energy traveling through the general target area 106. Other means of increasing the energy absorption include concentrating the signal on a localized area, or specific target area 130, and/or enhancing the energy absorption characteristics of the target area 130.

One method of inducing a higher temperature in the specific target area 130 includes using a reception head that is smaller than the transmission head. The smaller reception head picks up more energy due to the use of a high-Q resonant circuit described in more detail below. Optionally, an RF absorption enhancer 132 is used. An RF absorption enhancer is any means or method of increasing the tendency of the specific target area 130 to absorb more energy from the RF signal. Injecting an aqueous solution is a means for enhancing RF absorption. Aqueous solutions suitable for enhancing RF absorption include, for example, water, saline solution, aqueous solutions containing suspended particles of electrically conductive material, such as metals, e.g., iron, various combination of metals, e.g., iron and other metals, or magnetic particles. These types of RF enhancers (i.e., non-targeted "general RF enhancers") are generally directly introduced into the target area. Other exemplary general RF enhancers are discussed below, e.g., aqueous solutions of virtually any metal sulfate (e.g., aqueous solutions of iron sulfate, copper sulfate, and/or magnesium sulfate, e.g., aqueous solutions (about 5 mg/kg of body mass), copper sulfate (about 2 mg/kg of body mass), and magnesium sulfate (about 20 mg/kg of body mass)), other solutions of virtually any metal sulfate, injectable metal salts (e.g., gold salts), and RF absorbing particles attached to other non-targeted carriers. Preferably, these types of RF enhancers may be directly injected into the target area by means of a needle and syringe, or otherwise introduced into the patient.

Other means of enhancing RF absorption include providing targeted RF enhancers, such as antibodies with associated RF absorption enhancers, such as metal particles. The antibodies (and other targeting moieties, discussed below) target and bind to specific target cells in the target area 130. Generally, antibodies (and other targeting moieties) can be directed against any target, e.g., tumor, bacterial, fungal, viral, parasitic, mycoplasmal, histocompatibility, differentiation and other cell membrane antigens, pathogen surface antigens, toxins, enzymes, allergens, drugs and any biologically active molecules. Binding RF enhancing particles to the antibodies (and other carriers having at least one targeting moiety) permits the injection of the antibodies (and other carriers having at least one targeting moiety) into the patient and the targeting of specific cells and other specific targets. Once a high enough concentration of RF enhancers 132 are attached to the target cells, the RF signal 120 is passed through the specific target area 130. The RF enhancers induce the absorption of more energy, creating a localized temperature in the specific target area 130 that is higher than the temperature created in the general target area 106. In addition, a combination of antibodies (and other carriers having at least one targeting moiety) bound to different metals (and other RF absorbing particles, discussed below) can be used allowing for variations in the RF absorption characteristics in localized areas of the target areas. These variations in RF absorption characteristics permit intentional uneven heating of the specific target area 130.

Targeted RF enhancers and general RF enhancers can be used to improve current RF capacitive heating devices as well as current RF ablation devices. Antibodies bound to metals, which can act as RF absorption enhancers in accordance with the teachings of the present application, can be obtained through commercially available channels.

Targeted RF enhancers and general RF enhancers are applicable for both in-vivo and in-vitro applications. In one in-vitro application the targeted RF enhancers and/or general RF enhancers are in introduced into the target area prior to the target area being removed from the patient. After the targeted RF enhancers and/or general RF enhancers bind to the target area, the target area is removed from the patient and treated with one or more RF signals. In another in-vitro application the target area is removed from the patient before the RF enhancers are introduced into the target area. Once the target area is in a suitable vessel, the targeted RF enhancers and/or general RF enhancers are introduced into the target area. The target area is then treated with one or more RF signals.

Optionally, multiple frequency RF signals 120 are used. Multiple frequency RF signals can be used to treat target areas. Multiple frequency RF signals allow the energy absorption rate and absorption rate in different locations of the target area to be more closely controlled. The multiple frequency signals can be combined into one signal, or by use of a multi-plated transmission head, or multiple transmission heads, can be directed at one or more specific regions in the target area. This is useful for treating target areas that have specific regions of various shapes, thicknesses and/or depths. Similarly, pulsed RF signals, variable frequency RF signals and other combinations or variations of the RF signals can be used to more precisely control and target the heating of the specific target areas. These and other methods of increasing RF absorption can be used independently or in any number of combinations to increase the energy absorption rate of the specific target area 130.

In addition, antibodies (or other targeting moieties) bound with magnetic particles (i.e., magnetic targeted RF enhancers) can be steered to specific locations using magnets or magnetic resonant imaging (MRI) machines. Thus, the magnetic targeted RF enhancers can be directed toward specific target area or target cells. Furthermore, once the magnetic targeted RF enhancers bind to the specific target cells, the target cells can be separated from the other cells by use of a magnetic force. The magnetic force can be either an attracting force, or a repelling force. Magnets or MRI machines can also be used to steer injected (or otherwise introduced) magnetic particles to specific locations. The magnetic general RF enhancers discussed above may also be directed toward a specific target area or target cells using a magnetic force from, e.g., a magnet or MRI machine.

Additionally, in accordance with the teachings above, a target of RF induced hyperthermia may be specific target cells and need not be limited to a specific region of a body. Certain cancers, e.g., blood cancers, do not necessarily manifest themselves in a localized region. As discussed above, targeted RF enhancers, will target specific cells and need not be localized. In the case of blood cancers, such as lymphoma, leukemia, and multiple myeloma, such targeted RF absorption enhancers (e.g., targeting moieties bound to RF absorbing particles) can be introduced into a patient and then a selected region of the body (or perhaps the entire body) can be irradiated with RF energy, with the RF absorption enhancers bound to the cells heating up and heating those cells more than cells without RF absorption enhancers bound to them.

The above discussion recites several different types of exemplary RF absorption enhancers for enhancing the RF absorption of a target area (which may be a tumor or a portion of a tumor or target cells or some other target), such as (i) solutions and/or suspensions introduced into a target area to enhance RF heating of the target area (general RF absorption enhancers) and (ii) antibodies (or other targeting moieties) bound to RF absorbing particles that are introduced into a patient and that target specific target cells to enhance RF heating of the targeted cells (targeted RF absorption enhancers). As discussed above, these and other RF absorption enhancers may be used independently or in any number of combinations to increase RF absorption of a target area. The targeted RF absorption enhancers discussed herein can be thought of as effectively changing the resonant frequency of the target cells, i.e., adding another, artificial frequency to the target cells (which may be a resonant frequency of RF absorbing particles), because the RF absorbing particles, which are bound to target cells via the targeting moieties, will absorb more RF energy and heat more quickly than the target cells will at that frequency. Thus, instead of trying to determine one or more resonant frequencies of target cells, the targeted RF absorption enhancers used in accordance with the systems and methods of the present invention may be used to effectively add an artificial frequency or frequencies to the target cells at whatever artificial frequency or frequencies are desired to create hyperthermia.

The targeted RF absorption enhancers discussed above have a portion that binds to one or more targets and an associated portion that absorbs RF energy relatively well, e.g., a carrier having a targeting moiety and attached to an RF absorbing particle. The general RF absorption enhancers may also have an associated portion that absorbs RF energy relatively well e.g., a non-targeted carrier attached to an RF absorbing particle or RF absorbing particles in solution or suspension. Several examples given above of such RF absorbing particles listed above include particles of electrically conductive material, such as metals, iron, various combination of metals, irons and metals, or magnetic particles. Other examples are given below. Of course, these particles may be sized as so-called "nanoparticles" (microscopic particles whose size is measured in nanometers, e.g., 1-1000 nm) or sized as so-called "microparticles" (microscopic particles whose size is measured in micrometers, e.g., 1-1000 µm). If these particles are to be injected (or otherwise introduced) intravenously, such particles are preferably small enough to be bound to and carried with the at least one carrier to a target cell (e.g., in the patient's body) or target area (e.g., in the patient's body) via the patient's vascular system. In accordance with other exemplary embodiments of the present invention, other RF absorption enhancers may be used, e.g., using other carriers other than antibodies and/or using other RF absorbing particles than those specifically identified above.

Examples of such other carriers (both targeted and non-targeted) for RF absorption enhancers include any one or more of the following: biomolecules, biological cells, microparticle delivery systems, nanoparticle delivery systems, water-soluble polymers, other polymers, molecular or cellular proteomic or genomic structures, as well as other small particle constructs, including biological or robotic constructs, whether organic or from man-made materials, such as synthetic applied materials. Again, these carriers are attached to, or perhaps contain, RF absorbing particles to form RF absorption enhancers.

Exemplary biomolecules that may be used as carriers (both targeted and non-targeted) for RF absorption enhancers include any one or more of the following: organic molecules, nucleotides, proteins, antibodies, other specialized proteins, ligands, oligonucleotides, genetic material, nucleotides, DNA, RNA, viruses, retroviruses, organometallic molecules, proteins that are rapidly taken up by fast growing cells and tumors, transferrin, RGD (arg-gly-asp tripeptide) peptides, and NGR (asn-gly-arg tripeptide) peptides, folate, trasferrin, galactosamine, and GM-CSF (granulocyte macrophage colony stimulating factor). Herein, the term "organometallic molecule" (or just organometallics) means a molecule in which there is at least one bonding interaction (ionic or covalent, localized or delocalized) between one or more carbon atoms of an organic group or molecule and a main group, transition, lanthanide, or actinide metal atom (or atoms), and shall include organic derivatives of the metalloids (boron, silicon, germanium, arsenic, and tellurium), organic derivatives of all other metals and alloys, molecular metal hydrides; metal alkoxides, thiolates, amides, and phosphides; metal complexes containing organo-group 15 and 16 ligands; metal nitrosyls and similar others. Thus, in addition to being bound to separate RF absorbing particles to form RF absorption enhancers, some organometallic molecules may function as RF absorption enhancers by themselves, having both a carrier portion and an RF absorbing metallic portion. These organometallic molecules may be directly injected (or otherwise introduced) or may be attached to organic, biomolecular, biopolymer, molecular or cellular proteomic or genomic structures, or may be placed in biologic, robotic, or man-made synthetic applied materials. The application of organometallics in nuclear medicine (i.e. for the labeling of receptor binding biomolecules like steroid hormones or brain tracers) has been proposed in the literature. Technetium and radiogallium, typically used for medical imaging, can be modified with an organometallic. These biomolecules, organometallic technetium and organometallic radiogallium, could serve the dual function of imaging a tumor and be a radiofrequency enhancer because of their specific heat properties and imaging properties. Additionally, organometallic technetium and/or organometallic radiogallium may be bound to one or more different RF absorbing particles, e.g., bound to any one or more of virtually any of the RF absorbing particles described herein, to form RF absorption enhancers.

Exemplary biological cells (both targeted and non-targeted) that may be used as carriers for RF absorption enhancers include any one or more of the following: white blood cells, modified white cells, vaccine stimulated white cells, expanded white cells, T-cells, and tumor infiltrating lymphocytes (TILs). In general, these cells can be removed from a tumor or the circulating blood of a cancer patient and grown in tissue culture dishes or suspensions; thereafter, RF absorbing particles can be microinfused or absorbed into the cells to create RF absorption enhancers.

Exemplary microparticle and nanoparticle delivery systems (both targeted and non-targeted) that may be used as carriers for RF absorption enhancers include any one or more of the following: liposomes, immunoliposomes (liposomes bound to antibodies or antibody fragments or non-antibody ligand-targeting moieties), magnetic liposomes, glass beads, latex beads, other vesicles made from applied materials, organically modified silica (ORMOSIL) nanoparticles, synthetic biomaterial like silica modified particles and nanoparticles, other nanoparticles with the ability to take up DNA (or other substances) for delivery to cells, other nanoparticles that can act as a vector to transfer genetic material to a cell. Many of these can be directly taken up or otherwise internalized in the targeted cells. Liposomes are artificial microscopic vesicles used to convey substances—e.g., nucleic acids, DNA, RNA, vaccines, drugs, and enzymes—to target cells or organs. In the context of this application, liposomes may contain and carry RF absorbing particles (such as metal particles, organometalics, nanoparticles, etc.) to target cells or organs. These and other microparticle and nanoparticle delivery systems (both targeted and non-targeted) may be used to carry any one or combination of two or more of virtually any of the RF absorbing particles described herein, to form RF absorption enhancers. Exemplary polymers that may be used as carriers for RF absorption enhancers include any one or more of the following: dextran, albumin, and biodegradable polymers such as PLA (polylactide), PLGA polymers (polylactide with glycolide or poly(lactic acid-glycolic acid)), and/or hydroxypropylmethacrylamine (HPMA).

Other exemplary carriers for RF absorption enhancers include: molecular or cellular proteomic or genomic constructs, as well as other small particle constructs, including biological or robotic constructs, whether organic or from man-made materials, such as synthetic applied materials.

Targeted RF absorption enhancers are characterized by targeting and binding to target cells to thereby increase heating of target cells responsive to the RF signal by interaction between the RF signal and the targeted RF absorption enhancer. The target cells may be in an organ or a tumor or a portion of a tumor, or may be circulating or isolated cells, such as blood cells. Some targeted RF absorption enhancers may bind to the cell membrane or intracellular contents of (e.g., one or more biomolecules inside) the target cells. Some targeted RF absorption enhancers may bind to target cells by being taken up or otherwise internalized by the target cells. Some targeted RF absorption enhancers discussed herein can be thought of as effectively changing the resonant frequency of target cells, i.e., adding another, artificial frequency to the target cells (which may be a resonant frequency of RF absorbing particles), because the RF absorbing particles, which are bound to target cells via the targeting moieties, will absorb more RF energy and heat more quickly than the target cells will at that frequency. For targeted RF absorption enhancers, carriers with a targeting moiety for targeting and binding to a target cells ("targeted carriers") are attached (either directly or indirectly) to any of the RF absorbing particles described herein and introduced into the patient prior to transmitting the RF signal to create hyperthermia. Some targeted carriers for RF absorption enhancers (e.g., antibodies, ligands, and TILs) inherently have targeting moieties for targeting some part of target cells. Other RF absorption enhancer carriers (e.g., liposomes) may need to be modified to be targeting carriers by attaching one or more target moieties for targeting some part of target cells, e.g., immunoliposomes, which are liposomes bound to antibodies or antibody fragments or non-antibody ligand-targeting moieties. Some targeted carriers (e.g., antibodies, ligands, and antibody fragments) target one or more "target biomolecules" of target cells and bind to the target cells. The term "target biomolecules" as used herein means a molecular structure within a target cell or on the surface of a target cell characterized by selective binding of one or more specific substances. The term "target biomolecules" includes, by way of example but not of limitation, cell surface receptors, tumor-specific markers, tumor-associated tissue markers, target cell markers, or target cell identifiers, such as CD markers, an interleukin receptor site of cancer cells, and other biomolecules to which another molecule, e.g. a ligand, antibody, antibody fragment, cell adhesion site, biopolymer, synthetic biomaterial, sugar, lipid, or other proteomic or genetic engineered constructs including recombinant technique, binds. Examples of targeted carriers and other targeting moieties that can be used to create targeted RF absorption enhancer carriers include: bivalent constructs, bispecific constructs, fusion proteins; antibodies; antibody fragments; non-antibody ligands; and non-antibody targeting moieties (e.g., GM-CSF which targets to GM-CSF receptor in leukemic blasts or Galactosamine which targets endothelial growth factor receptors in the vessels).

Tumors may produce antigens recognized by antibodies. There are currently trials of antibodies and antibody fragments for virtually all cancers and others are being developed. Tumors often express high levels and/or abnormal forms of glycoproteins and glycolipids. Antibodies are known to target these (e.g., Anti-MUC-1 for targeting breast or ovarian cancer). Oncofetal antigens are also produced by some tumors. Antibodies are known to target these (e.g., anti-TAG72 [anti-tumor-associated glycoprotein-72] for targeting colonrectal, ovarian and breast cancer or anti-CEA [anti-carcinoembryonic antigen] for targeting colon-rectal, small-cell lung and ovarian cancers). Tissue specific antigens have also been targeted. Antibodies are known to target these (e.g., anti-CD25 for targeting interleukin-2 receptor in cutaneous T-cell lymphoma). The rapid production of blood vessels in tumors presents another target. Antibodies are known to target these (anti-VEGR [anti-vascular endothelial growth-factor receptor] for targeting endothelial cells in solid tumors. These are but a few examples of the antibodies have already been used as ligands in targeted therapy to which the present RF enhancers could be attached. Any one or more of the RF absorbing particles disclosed herein can be attached (directly or indirectly) to any of these antibodies and antibody fragments (and any others) to form substances that may be used as targeted RF absorption enhancers in connection with hyperthermia generating RF signals in accordance with the teachings herein.

Other examples of known ligand antibodies are the monoclonal antibodytrastuzumab (Herceptin) which targets to ERBB2 receptor in cells that over-express this receptor such as breast and ovarian cancers or rituximab an anti-CD 20 which targets cell surface antigen in non-hodgkin's lymphoma and other b-cell lymphoproliferative diseases. Any one or more of the RF absorbing particles can be attached (directly or indirectly) to any of these antibodies and antibody fragments (and any others) to form substances that may be used as targeted RF absorption enhancers in connection with hyperthermia generating RF signals in accordance with the teachings herein.

For general RF absorption enhancers, non-targeted carriers, such as certain biomolecules, oligonucleotides, certain cells (such as cells having general adhesive molecules on their surfaces that are less specific than ligands and antibodies, which general adhesive molecules may attach to many different types of cells), etc. may be attached (either directly or indirectly) to any of the RF absorbing particles described herein and injected (or otherwise introduced) prior to transmitting the RF signal to create hyperthermia. Nanoparticles having oligonucleotides attached thereto, such as DNA sequences attached to gold nanoparticles, are available from various sources, e.g., Nanosphere, Inc., Northbrook, Ill. 60062, U.S. Pat. No. 6,777,186.

Figure 24:
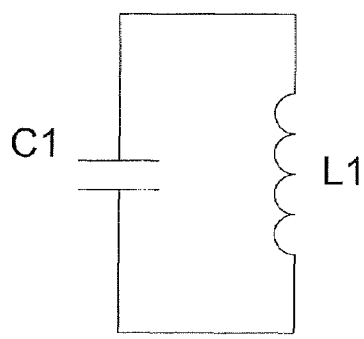
FIGS. 24-29 are schematic circuit diagrams of exemplary tuned circuit RF absorbing particles for RF absorption enhancers.
Figure 25:
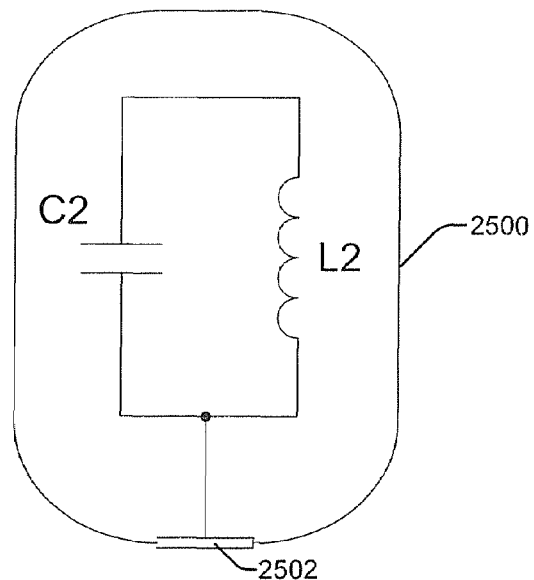
Figure 26:
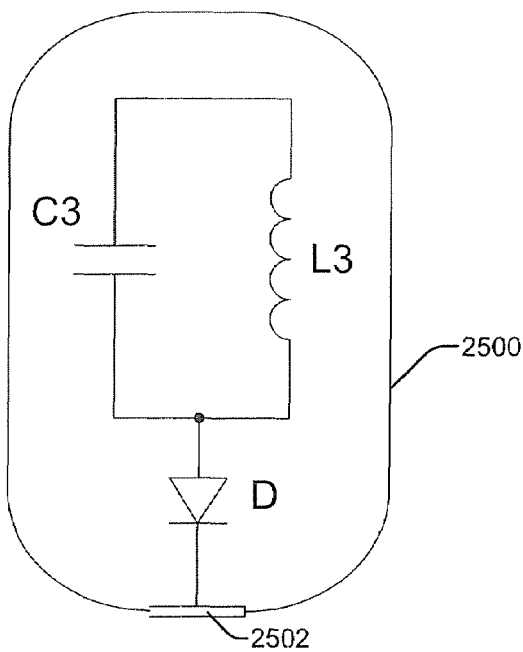
Figure 27:
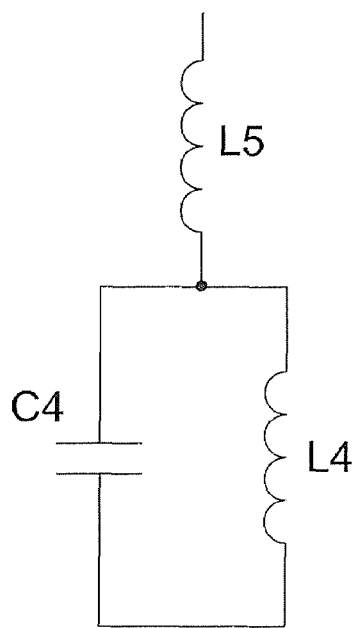
Figure 28:
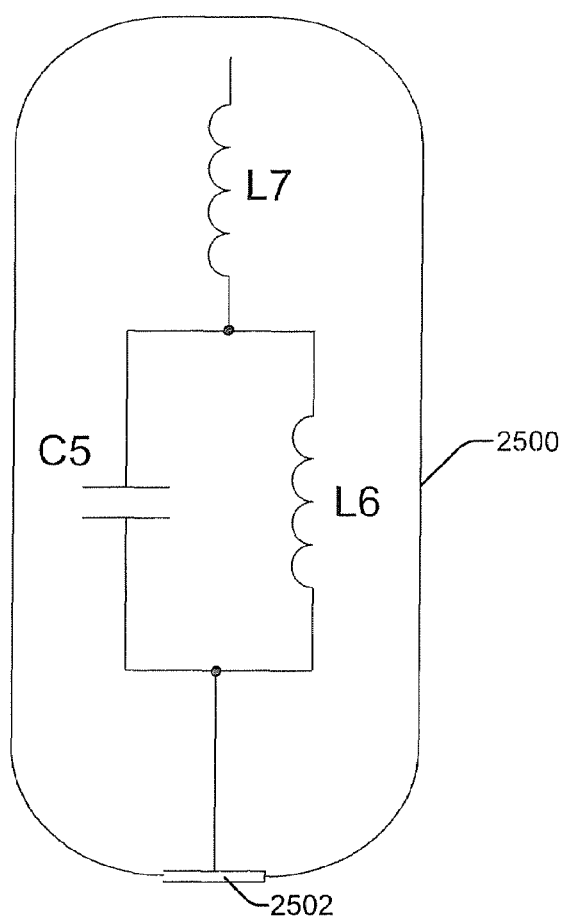
Figure 29:
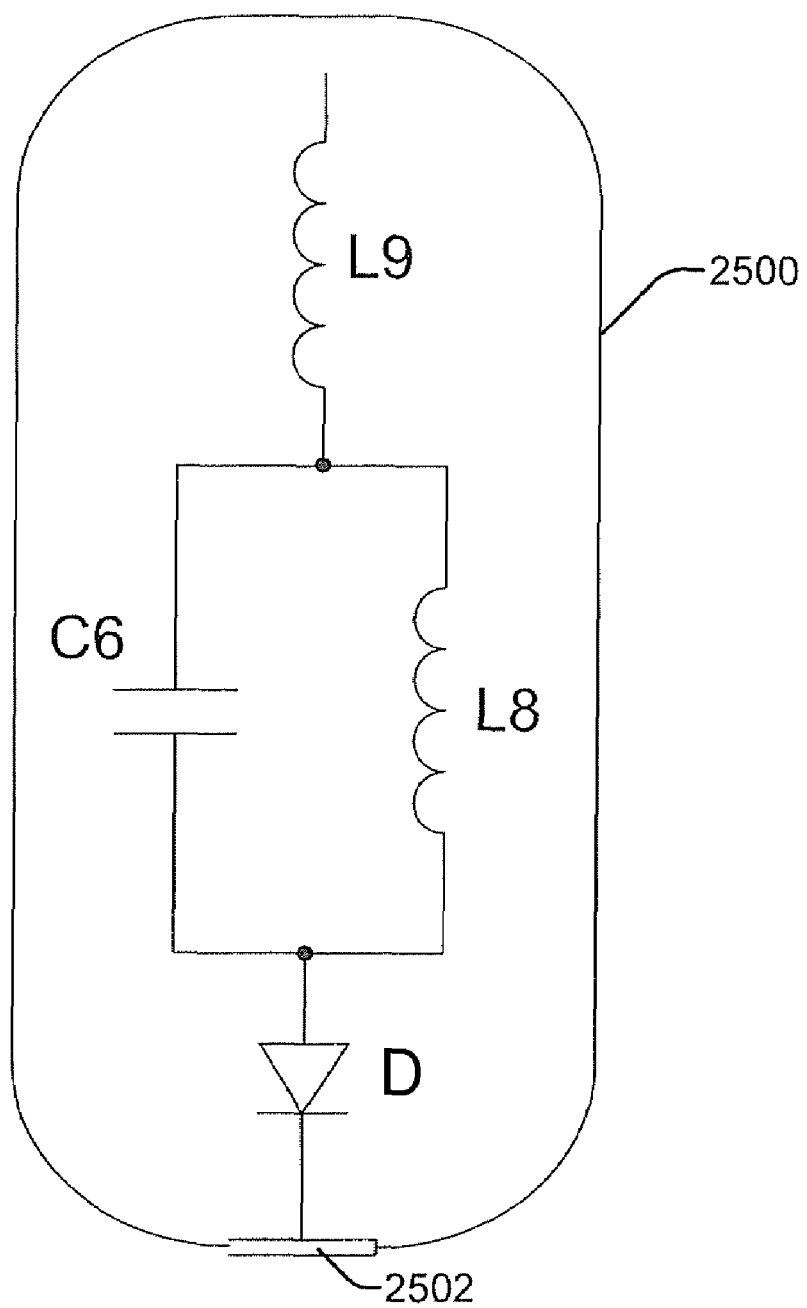
Figure 30:
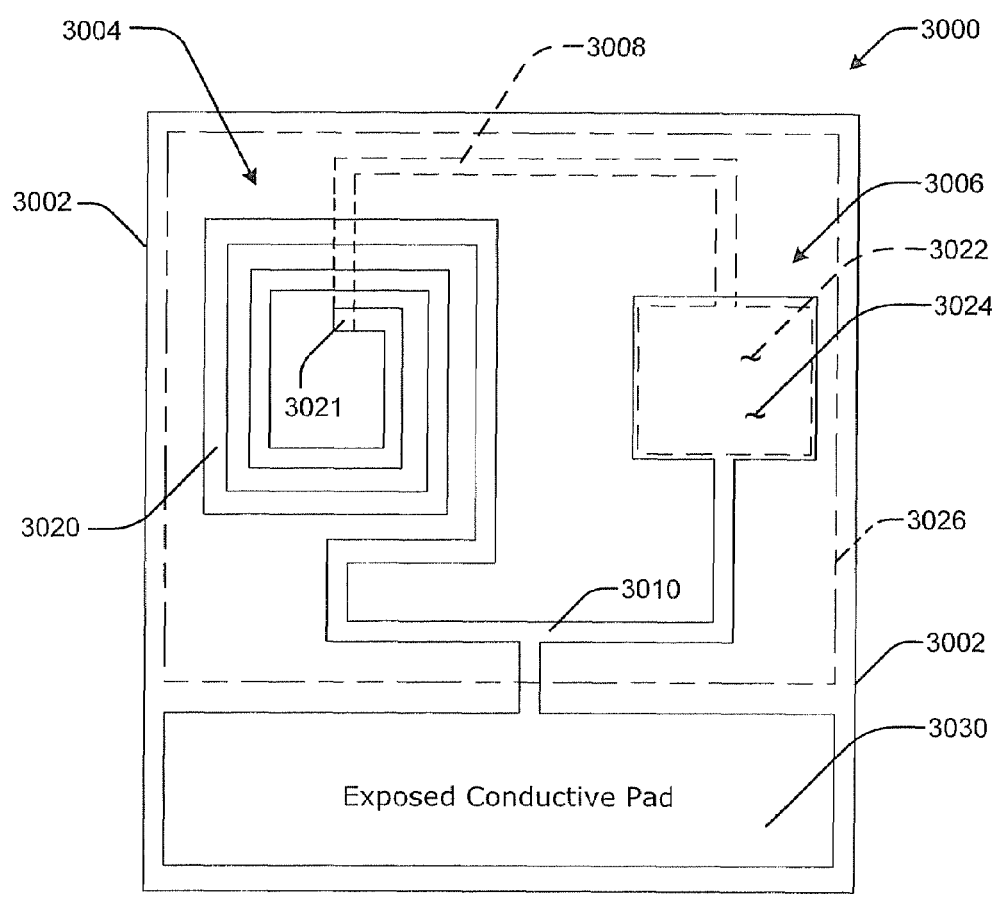
FIGS. 30-33 are schematic illustrations of exemplary implementations of tuned circuit RF absorbing particles for RF absorption enhancers.
Figure 31:
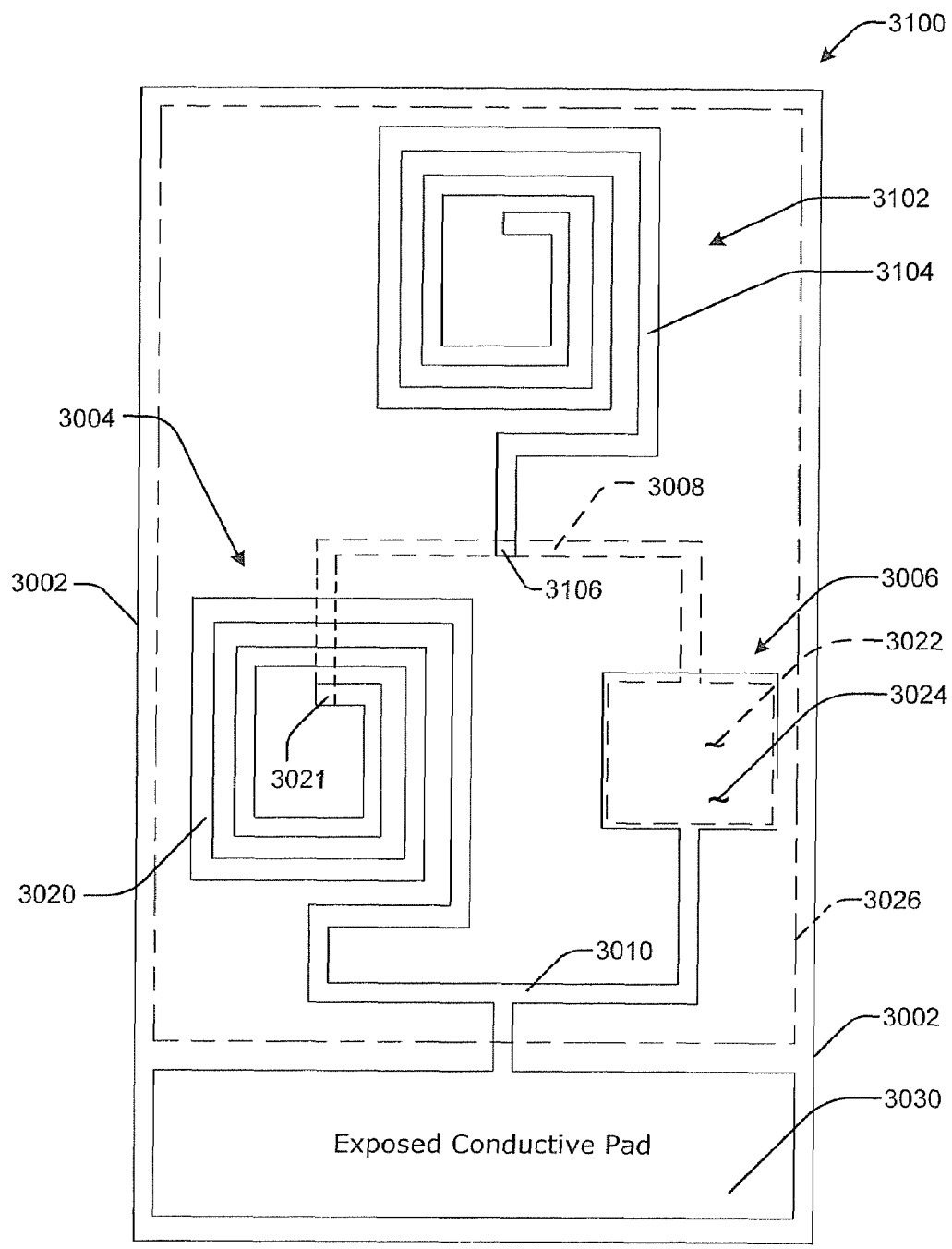
Figure 32:
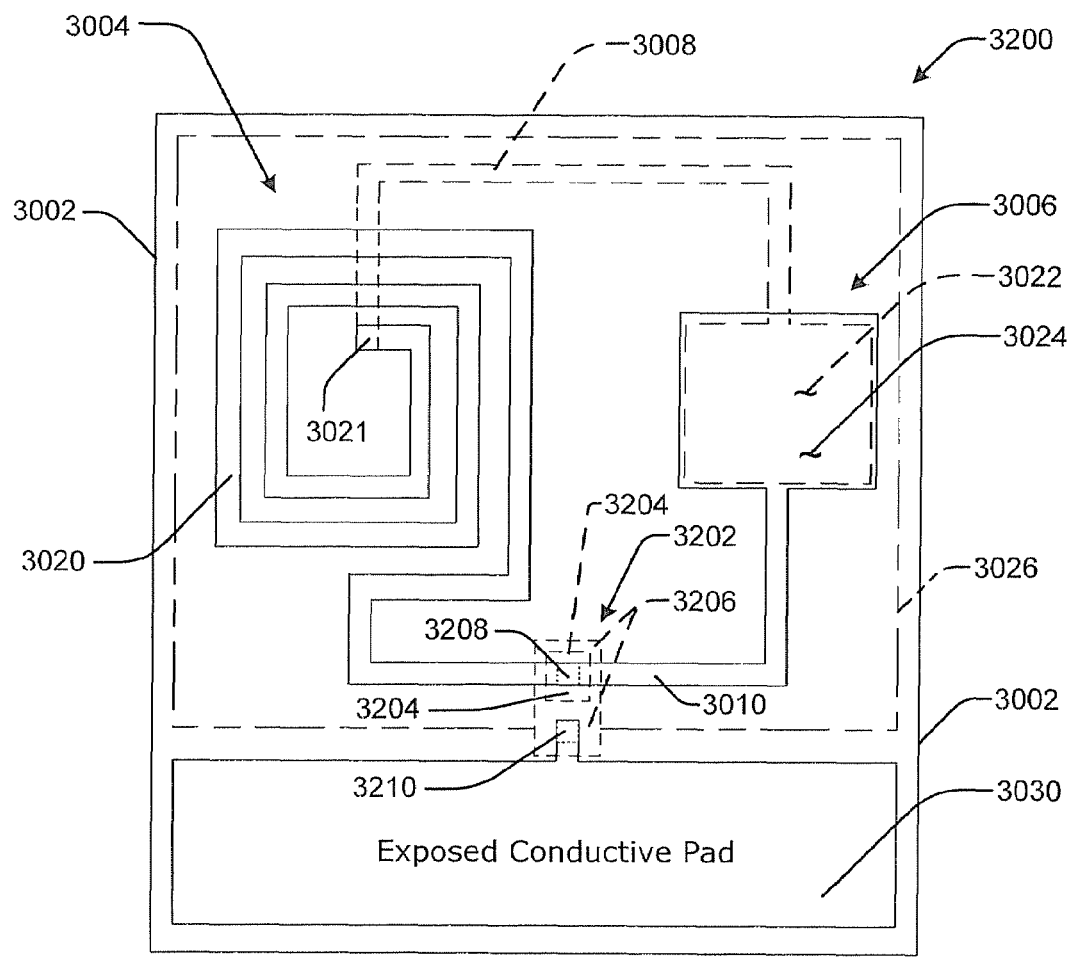
Figure 33:
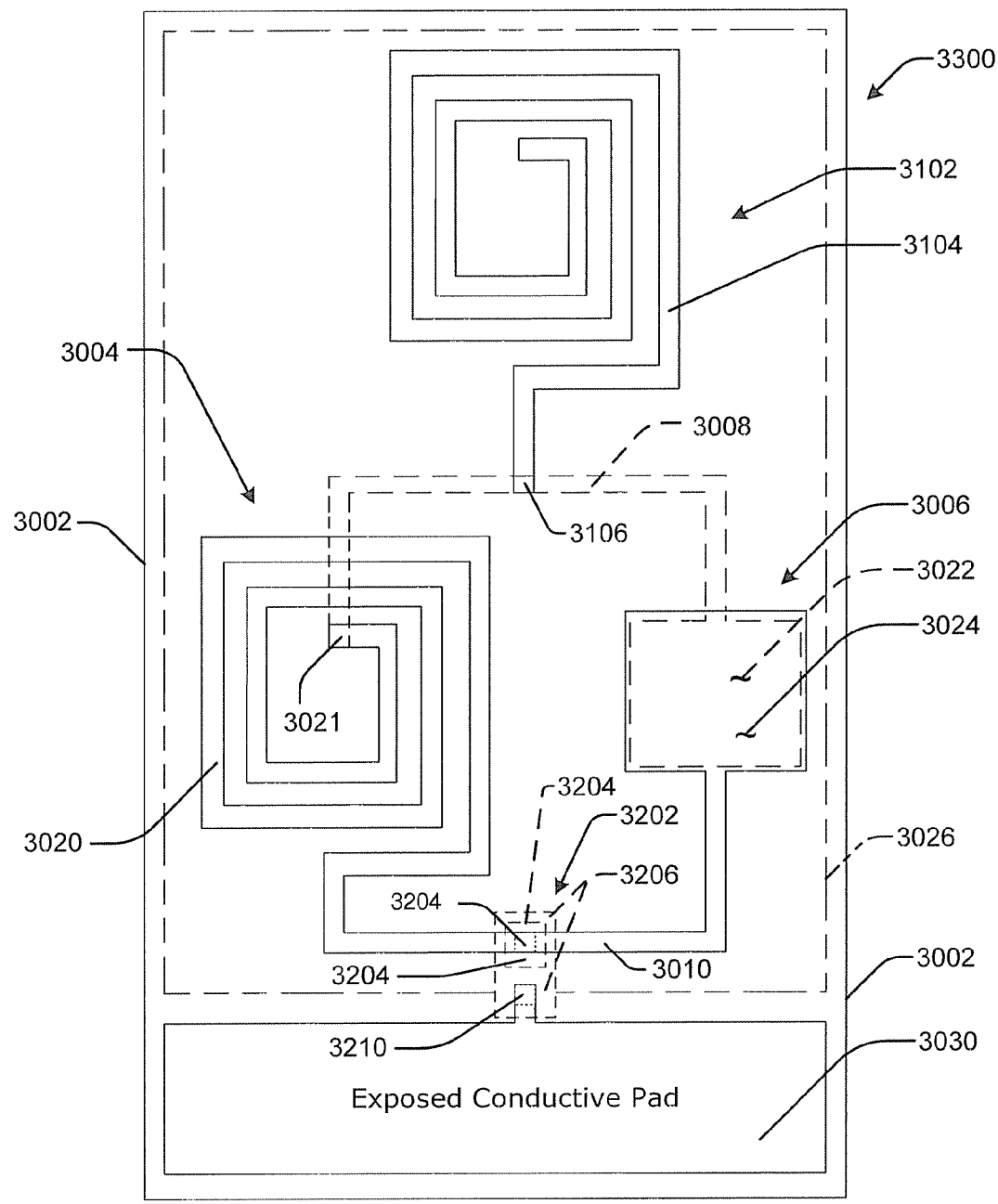

RF absorbing particles are particles that absorb one or more frequencies of an RF electromagnetic signal substantially more than untreated cells in or proximate the target area. This permits the RF signal to heat the RF absorbing particle (or a region surrounding it or a cell near it) substantially more than untreated cells in or proximate the target area, e.g., heating the RF absorbing particles (or a region surrounding them or a cell near them) with the RF signal to a temperature high enough to kill target cells bound to them (or damage the membrane of target cells bound to them), while untreated cells in or proximate the target area are not heated with the RF signal to a temperature high enough to kill them. Exemplary target hyperthermia temperatures include values at about or at least about: 43° C, 106.3° F., 106.5° F., and 106.7° F., and 107° F. It may also be desirable to generate a lower hyperthermia temperature (e.g., any temperature above 103°, or above 104°, or above 105°) which may not directly cause necrosis from hyperthermia within the target area, but may kill or damage cells in the target area in combination with another therapy, e.g., chemotherapy and/or radiotherapy and/or radioimmunotherapy. Pulsed RF signals may produce very localized temperatures that are higher. Exemplary RF absorbing particles mentioned above include particles of electrically conductive material, such as gold, copper, magnesium, iron, any of the other metals, and/or magnetic particles, or various combinations and permutations of gold, iron, any of the other metals, and/or magnetic particles. Examples of other RF absorbing particles for general RF absorption enhancers and/or targeted RF absorption enhancers include: metal tubules, particles made of piezoelectric crystal (natural or synthetic), very small LC circuits (e.g., parallel LC tank circuits, FIGS. 24 and 30), tuned radio frequency (TRF) type circuits (e.g., a parallel LC tank circuit having an additional inductor with a free end connected to one of the two nodes of the tank circuit, FIGS. 27 and 31), other very small tuned (oscillatory) circuits (e.g., FIGS. 25, 26, 28, 29, and 32-33), hollow particles (e.g., liposomes, magnetic liposomes, glass beads, latex beads, other vesicles made from applied materials, microparticles, microspheres, etc.) containing other substances (e.g., small particles containing argon or some other inert gas or other substance that has a relatively high absorption of electromagnetic energy), particles of radioactive isotopes suitable for radiotherapy or radioimmunotherapy (e.g., radiometals, β-emitting lanthanides, radionuclides of copper, radionuclides of gold, copper-67, copper-64, lutetium-177, yttrium-90, bismuth-213, rhenium-186, rhenium-188, actinium-225, gold-127, gold-128, In-111, P-32, Pd-103, Sm-153, TC-99m, Rh-105, Astatine-211, Au-199, Pm-149, Ho-166, and Thallium-201 thallous chloride), organometallics (e.g., those containing Technetium 99m and radiogallium), particles made of synthetic materials, particles made of biologic materials, robotic particles, particles made of man made applied materials, like organically modified silica (ORMOSIL) nanoparticles. These particles may be sized as so-called "nanoparticles" (microscopic particles whose size is measured in nanometers, e.g., 1-1000 nm) or sized as so-called "microparticles" (microscopic particles whose size is measured in micrometers, e.g., 1-1000 μm). These particles are preferably small enough to be bound to and carried with the at least one biomolecule to a target cell via the patient's vascular system. For example, gold nanospheres having a nominal diameter of 3-37 nm, plus or minus 5 nm may used as RF absorption enhancer particles. Some of the radioactive isotopes are inserted as "seeds" and may serve as RF absorption enhancers, e.g., palladium-103, to heat up a target area in the presence of an RF signal.

In the case of the particles of radioactive isotopes used for various treatments, e.g., to treat cancer, a multi-step combination therapy can be used in accordance with the teachings hereof. In a first phase, targeted carriers (either carriers with an inherent targeting moiety or non-targeting carriers with a targeting moiety attached thereto) are attached to one or more RF absorbing radionuclides, such as any of the radiometals mentioned herein, are introduced into the patient, target specific cells, and emissions (e.g., alpha emissions and/or beta emissions and/or Auger electron emissions) therefrom damage or kill the targeted cells. This first phase may include the introduction of other radiometal-labeled antibodies that may act as RF absorption enhancers but that do not have cell damaging emissions, e.g., radiometals used primarily for imaging. This first phase, in the context of certain antibodies and certain radioisotopes, is known to those skilled in the art. Thereafter, in a second phase according to the present invention, an RF signal is transmitted in accordance with the teachings herein to generate a localized hyperthermia at the targeted cells by using the radioisotope particles (which may be partially depleted) as RF absorption enhancing particles. Such a two-phase therapy may result in enhanced treatment effectiveness vis-à-vis traditional radioimmunotherapy with the addition of the second RF-induced hyperthermia phase. In the alternative, such a two-phase therapy may result in about the same treatment effectiveness vis-à-vis traditional radioimmunotherapy by using a lower dose of radioisotope emissions in the first phase (some radioisotopes can cause severe damage to tissue, e.g., bone marrow, during radiotherapy) with the addition of the second RF-induced hyperthermia phase. Between the two phases, one may wait for a predetermined period of time, e.g., a period of time based on the half-life of emissions from a particular radiometal used, or a period of time based on a patient recovery time after the first phase, or a period of time based on the ability of one or more non-targeted organs (e.g., the liver or kidneys) to excrete, metabolize, or otherwise eliminate the radioimmunotherapy compound(s). In this regard, it may be beneficial for this multiphase therapy to use radiometals or other RF absorbing radionuclides with a relatively high residualization in target cells. This may help prevent damage to non-targeted organs and cells by permitting them to excrete, metabolize, or otherwise eliminate the radioimmunotherapy compound(s) prior to coupling a hyperthermia generating RF signal using the radioimmunotherapy compound as an RF enhancer. For example, a patient treated with Yttrium-90 (Y-90) ibritumomab tiuxetan (Y-90 ZEVALIN®) (which is used to treat b-cell lymphomas and leukemias) in accordance with known protocols, and also perhaps injected with Indium-111 (In-111) ibritumomab tiuxetan (In-111 ZEVALIN®) (which is used for imaging in connection with rituximab treatments), may also thereafter have a hyperthermia-generating RF signal coupled through a body part to heat the cells targeted by the Y-90 ZEVALIN® and/or the (In-111 ZEVALIN®). Particles of radioactive isotopes used to treat cancer, either attached to biomolecules or not, can be obtained from various commercial sources. Radiometals can be attached to monoclonal antibodies, e.g., 90-Yttrium-ibritumomab tiuxetan [Zevalin] or 131-iodine-tositumomab (Bexxar) target anti-CD 20 antigens and are used for lymphomas. Radiofrequency can produce an added effect with these metals.

Very small LC circuits and other tuned (oscillatory) circuits were mentioned above as exemplary RF absorbing particles. The very small LC circuits and other tuned (oscillatory) circuits (FIGS. 24-29) may damage target cells with vibration (i.e., heating) when a signal at or near the resonant frequency of the tuned circuit is received. Additionally, or in the alternative, there may be direct radio frequency ablation to the cell from RF energy absorbed by tuned circuit RF absorbing particles, which current may be transferred to target cells via one or more metal connections of the tuned circuit particles to the cell membrane or cell itself (see the discussion below with respect to the at least one exposed electrical contact 2502 and the encapsulating electrically conducting material).

For purposes of the present application, virtually any of the carriers (targeted or non-targeted) for RF absorption enhancers described herein may be attached (either directly or indirectly) to virtually any RF absorbing particle described herein and/or virtually any combination of and/or permutation of any RF absorbing particles described herein to form any one or more RF absorption enhancers. For example, antibody carriers may be bound to (or otherwise carry) one or more piezoelectric crystals, tuned electronic circuits, tuned RF (TRF) circuits, TRF circuits having a rectifier D (FIG. 29), LC tank circuits, LC tank circuits having a rectifier D (FIG. 26), metallic particles, and/or metallic nanoparticles. As other examples, TIL carriers may be attached to or contain an organometallic or TRF or any other of the microscopic electronic circuit particles, RNA or DNA carriers may be attached to organometallic molecules acting as RF absorbers, antibody carriers may be attached to organometallic molecules acting as RF absorbers, metals (e.g., iron) may be attached to transferrin, liposomes may contain RF absorbing particles, immunoliposomes (liposomes bound to antibodies or antibody fragments or non-antibody ligand-targeting moieties) may contain RF absorbing particles, immunopolymers (microreservoirs) formed by linking therapeutic agents and targeting ligands to separate sites on water-soluble biodegradable polymers, such as HPMA, PLA, PLGA, albumin, and dextran, may be used to form RF absorption enhancers by attaching to an RF absorbing particle and a targeting moiety (antibody or non-antibody), those formed by the attachment of multivalent arrays of antibodies, antibody fragments, or other ligands to the liposome surface or to the terminus of hydropic polymers, such as polyethylene glycol (PEG), which are grafted at the liposome surface) may contain RF absorbing particles, dextran may have metallic particles and targeting peptides attached to it, polymers of HPMA can have targeting peptides and metallic particles attached, liposomes may carry metallic or thermally conductive synthetic biomaterials inside, immunoliposomes may carry metallic or thermally conductive synthetic biomaterials inside, monoclonal antibodies and metals, monoclonal antibodies and radioisotopes like Zevalin, antibody fragments and organometallics, antibody fragments and radioisotopes, fusion proteins and organometallics, fusion proteins and radioisotopes, bispecifics and metals or organometallics, bispecifics and bivalents constructs and radioisotopes. Since tumor penetration is often hampered by particle size, reductionistic engineering techniques that create smaller proteomic and genomic constructs and recombinations which are more tumor-specific will be able to carry RF absorption enhancers. As other examples, microparticle and nanoparticle delivery systems (both targeted and non-targeted) and any of the other carriers herein may carry two or more different RF absorbing particles, e.g., metallic particles of two different sizes, metallic particles and electronic circuits, metallic particles and an RF absorbing gas, electronic circuits and an RF absorbing gas, etc. Such combinations of RF absorbing particles may provide enhanced absorption at two different frequencies, e.g., two different resonant frequencies, or a resonant frequency and a frequency range (as one might see with a tuned RF circuit absorbing particle combined with a general particle, such as a metal particle), which may facilitate multilevel treatments at multiple tissue depths.

Additionally, virtually any of the foregoing RF absorbing particles may be partially encapsulated or fully encapsulated in a carrier or other encapsulating structure such as: glass beads, latex beads, liposomes, magnetic liposomes, other vesicles made from applied materials, etc. As exemplified by the tank circuit of FIG. 25 and the TRF circuit of FIG. 28, RF absorbing particles in the form of a tuned circuit may be partially encapsulated in an electrically insulating material 2500 (e.g., a glass or latex bead) and have at least one exposed electrical contact 2502 in circuit communication with the rectifier D for contact with biological material in the target area. In the alternative, RF absorbing particles in the form of a tuned circuit may be encapsulated in an electrically conducting material in circuit communication with the rectifier for contact with biological material in the target area. Similarly, as exemplified by the rectifying tank circuit of FIG. 26 and the rectifying TRF circuit of FIG. 29, RF absorbing particles having a rectifier D to rectify a received RF signal may be partially encapsulated in an electrically insulating material 2500 and have at least one exposed electrical contact 2502 in circuit communication with the rectifier D for contact with biological material in the target area to provide a path for rectified current to flow and perhaps damage cells and/or heat cells in the target area. In the alternative, RF absorbing particles having a rectifier to rectify a received RF signal may be encapsulated in an electrically conducting material in circuit communication with the rectifier for contact with biological material in the target area to provide a path for rectified current to flow and perhaps damage cells and/or heat cells in the target area. These may be fabricated using standard monolithic circuit fabrication techniques and/or thin film fabrication techniques. Various techniques for fabricating microscopic spiral inductors of FIGS. 24-29 using monolithic circuit fabrication techniques and/or thin film fabrication techniques are known, e.g., U.S. Pat. Nos. 4,297,647; 5,070,317; 5,071,509; 5,370,766; 5,450,263; 6,008,713; and 6,242,791. Capacitors and rectifiers D may also be fabricated using monolithic circuit fabrication techniques and/or thin film fabrication techniques (e.g., with a pair of conductive layers with a dielectric therebetween and a P-N junction, respectively). Thus, it is believed that the microscopic (preferably microparticle or nanoparticle) circuits of FIGS. 24-29 may be fabricated using known monolithic circuit fabrication techniques and/or thin film fabrication techniques. FIGS. 30-33 show exemplary embodiments of some exemplary tuned (oscillatory) circuit particles. FIG. 30 shows an exemplary embodiment 3000 of an LC particle of FIG. 25. The exemplary LC particle 3000 comprises a substrate 3002 carrying an inductor 3004 in circuit communication with a capacitor 3006 via conductive traces 3008, 3010. The inductor 3004 may be a spiral 3020 of electrically conductive material. The capacitor 3006 may be formed from two spaced plates 3022, 3024 of electrically conductive material with a dielectric (not shown) therebetween. Plate 3022 and conductive path 3008 are shown as at a lower level than plate 3024 and inductor 3020. Conductive path 3008 is connected to inductor 3020 with a via 3021. The encapsulating electrically insulating material 2500 in FIG. 20 may be implemented by a layer of electrically insulating material 3026 covering at least the inductor 3004 and the capacitor 3006 above in cooperation with the substrate 3002 below. The exposed electrical contact 2502 in FIG. 25 may be implemented as an exposed pad 3030 of conductive material. FIG. 31 shows an exemplary embodiment 3100 of a TRF circuit of FIG. 28. Particle 3100 may be the same as particle 3000, except particle 3100 has an additional inductor 3102. The inductor 3102 may be a spiral 3104 of electrically conductive material, in circuit communication by a via 3106 with the node 3008 connecting inductor 3004 and capacitor 3006. FIG. 32 shows an exemplary embodiment 3200 of a rectifying tank circuit 3200 of FIG. 26. Particle 3200 may be the same as particle 3000, except particle 3200 has a rectifier 3202. Rectifier 3202 may be implemented with a n-type semiconductor region (or a p-type region) 3204 in circuit communication with a p-type region (or an n-type region) 3206 as known to those in the art. The node 3010 connecting inductor 3004 and capacitor 3006 may be connected to rectifier 3202 at via 3208. Similarly, the exposed pad 3030 may be connected to rectifier 3202 at via 3210. FIG. 33 shows an exemplary embodiment 3300 of a rectifying TRF circuit of FIG. 28. Particle 3300 may be the same as particle 3100, except particle 3300 has a rectifier 3202. As with the rectifier in FIG. 32, rectifier 3202 may be implemented with an n-type semiconductor region (or a p-type region) 3204 in circuit communication with a p-type region (or an n-type region) 3206 as known to those in the art. The node 3010 connecting inductor 3004 and capacitor 3006 may be connected to rectifier 3202 at via 3208. Similarly, the exposed pad 3030 may be connected to rectifier 3202 at via 3210. The particles made of piezoelectric crystal can be obtained from various commercial sources, e.g., Bliley Technologies, Inc., Erie, Pa. Gases in the noble gas family, e.g., neon, argon, etc., exhibit relatively large excitation at relatively low RF signal strengths. The small particles containing argon can be obtained from various commercial sources.

Various means for getting the RF absorption enhancers of the present invention to the targeted cell site are contemplated. RF absorption enhancers may be introduced as part of a fluid directly into the tumor (e.g., by injection), introduced as part of such a fluid into the patient's circulation (e.g., by injection), mixed with the cells outside the body (ex-vivo), inserted into target cells with micropipettes. Nanoparticle RF absorption enhancers may be introduced by aerosol inhalers, sublinqual and mucosal absorption, lotions and creams, and skin patches. RF absorption enhancers may be directly injected into a patient by means of a needle and syringe. In the alternative, they may be injected into a patient via a catheter or a port. They may be injected directly into a target area, e.g., a tumor or a portion of a tumor. In the alternative, they may be injected via an intravenous (IV) system to be carried to a target cell via the patient's vascular system. RF absorption enhancers of the present invention may bind with the cell surface, bind to a target cell wall (e.g., those using monoclonal antibodies as a carrier) or be internalized by the cells (e.g., those using liposomes and nanoparticles as a carrier). Certain RF absorption enhancers of the present invention (e.g., those using TILs as a carrier) may be internalized by target cells. Additionally, it may be desirable to surgically-place certain RF absorption enhancers in a patient, e.g., metallic radioactive "seeds."

RF hyperthermia generating signal may have a frequency corresponding to a selected parameter of an RF enhancer, e.g., 13.56 MHz, 27.12 MHz, 915 MHz, 1.2 GHz. Several RF frequencies have been allocated for industrial, scientific, and medical (ISM) equipment, e.g.: 6.78 MHz±15.0 kHz; 13.56 MHz±7.0 kHz; 27.12 MHz±163.0 kHz; 40.68 MHz±20.0 kHz; 915 MHz±13.0 MHz; 2450 MHz±50.0 MHz. See Part 18 of Title 47 of the Code of Federal Regulations. It is believed that hyperthermia generating RF signals at sequentially higher frequency harmonics of 13.56 MHz will penetrate into respectively deeper tissue, e.g., a hyperthermia generating RF signal at 27.12 MHz will penetrate deeper than at 13.56 MHz, a hyperthermia generating RF signal at 40.68 MHz will penetrate deeper than at 27.12 MHz, a hyperthermia generating RF signal at 54.24 MHz will penetrate deeper than at 40.68 MHz, a hyperthermia generating RF signal at 67.80 MHz will penetrate deeper than at 54.24 MHz, a hyperthermia generating RF signal at 81.36 MHz will penetrate deeper than at 67.80 MHz, and so on (up to higher RF frequencies that may heat the skin uncomfortably or burn the skin). The optimum depth level is selected based upon antibodies used, and the physical size of the patient, the location and depth of the target area, and the tumor involved. As discussed above, combinations of two or more different frequencies may be used, e.g., a lower frequency RF component (such as 13.56 MHz) and a higher frequency component (such as 40.68 MHz) to target different tissue depths with the same hyperthermia generating RF signal.

Some of the exemplary particles shown comprise a rectifier D, e.g., FIGS. 26, 29, 32 and 33. Any of the RF absorption enhancer particles disclosed herein may also comprise an associated rectifier or demodulator (e.g., a diode or crystal in circuit communication with an oscillatory circuit) on some or all of the particles to cause rectification of the RF signal and thereby generate a DC current to damage the target cell(s) (in the case of targeted RF absorption enhancers) and/or cells in the target area (in the case of general RF absorption enhancers). Thus, for example, the particles may have an LC tank circuit with a diode (FIG. 26), a TRF (Tuned Radio Frequency) type circuit implemented thereon with a diode (FIG. 29) or a piezoelectric crystal with a diode. Such RF absorption enhancer particles may require the patient to be grounded, e.g., with a grounded lead pad, to provide a current path for the rectified RF current. These examples immediately above may be thought of as being similar to a simple TRF crystal set, which was powered only by a received RF signal and could demodulate the received signal and generate enough energy to power a high-impedance earphone with no outside power source other than the signal from the radio station. With the particles of the present application, the addition of a diode to these circuits may cause DC currents to flow within the target area and/or within and/or between the target cells responsive to the RF signal causing additional heating effect to generate the desired hyperthermia temperature, e.g., 43° C. The rectifier in any of these particles may be a single diode in either polarity (for half-wave rectification of the received RF signal) or a pair of diodes with opposite polarity (for full wave rectification of the RF signal).

Any of the RF absorbing particles described herein may be used alone or in virtually any combination of and/or permutation of any of the other particle or particles described herein. For example, it may be beneficial to use the same targeted carrier or targeting moiety with a plurality of different RF absorbing particles described herein for treatment of a target area. Similarly, any of the RF absorbing particles described herein may be used alone or in virtually any combination of and/or permutation of any of the targeting moieties or targeted carriers described herein. Similarly, it may be best for some target areas (e.g., some tumors) to use multiple different targeting moieties or targeted carriers in RF absorption enhancers, e.g., for a malignancy that may have different mutations within itself. Accordingly, virtually any combination or permutation of RF absorption enhancer targeting moieties or RF absorption enhancer targeted carriers may be attached to virtually any combination of and/or permutation of any RF absorbing particle or particles described herein to create RF absorption enhancers for use in accordance with the teachings herein.

Of the RF absorbing particles mentioned herein, some may be suitable for a 13.56 MHz hyperthermia-generating RF signal, e.g., gold nanoparticles, copper nanoparticles, magnesium nanoparticles, argon-filled beads, aqueous solutions of any of the metal sulfates mentioned herein, other hollow nanoparticles filled with argon, and any of the organometallics. RF absorption enhancers using these RF absorbing particles are also expected to be effective at slightly higher frequencies, such as those having a frequency on the order of the second or third harmonics of 13.56 MHz.

Some of the particles used in general RF absorption enhancers and/or targeted RF absorption enhancers may have one or more resonant frequencies associated therewith such that RF energy or other electromagnetic energy at that resonant frequency causes much greater heating of the particle than other frequencies. Thus, in accordance with the systems and methods of the present invention, it may be beneficial to match one or more resonant frequencies of RF absorption enhancer particles (general and/or targeted) with one or more of the electromagnetic frequencies being used to create hyperthermia. Additionally, the size of nanoparticles can vary to within certain manufacturing tolerances, with generally increased cost for a significantly smaller manufacturing tolerance. Thus, for a single frequency being used to create hyperthermia, there may be a nominal size of nanoparticles associated with that one frequency (e.g., a nominal size of nanoparticles having a resonant frequency at that frequency); however, the cost of manufacturing nanoparticles only at that one size might be prohibitively high. Consequently, from a cost standpoint, it might be beneficial (i.e., lower cost) to use nanoparticles with a larger size tolerance as RF absorption enhancer particles; however, the particles within a sample of nanoparticles with a larger size tolerance may have widely different resonant frequencies. Accordingly, it may be beneficial to use a frequency modulated (FM) signal to create hyperthermia with certain energy absorption enhancer particles. The parameters of the FM signal used to generate hyperthermia may be selected to correspond to the specific sample of particles being used as energy absorption enhancer particles. The center frequency of an FM hyperthermia generating signal may correspond to a resonant frequency of nominally sized particles used as energy absorption enhancer particles and the modulation of the FM hyperthermia generating signal may correspond to the size tolerance of the particles used as energy absorption enhancer particles. For example, a hyperthermia generating RF signal may be modulated with an FM signal having a frequency deviation of 300-500 KHz or more, and any particles having a resonant frequency within the FM deviation would vibrate and cause heating. Targeted RF absorption enhancer particles used in accordance with an FM signal used to generate hyperthermia can be thought of as effectively changing the resonant frequency range of the target cells, i.e., adding a resonant frequency range to the target cells. Thus, instead of trying to determine one or more resonant frequency ranges of target cells, in accordance with the systems and methods of the present invention the resonant frequency range of target cells may be effectively changed to whatever frequency range is desired to create hyperthermia. With all the embodiments described herein, one may select a frequency or frequency range for a signal used to generate hyperthermia that corresponds to a parameter of energy enhancing particles, or one may select energy enhancing particles corresponding to a frequency or frequency range for a signal used to generate hyperthermia. It may be beneficial to modify other existing thermotherapy devices to use the FM hyperthermia generating RF signal discussed herein. Similarly, it may be beneficial to modify other existing thermotherapy therapies to use the FM hyperthermia generating RF signal discussed herein.

Additionally, in any of the embodiments discussed herein, the RF signal used to generate hyperthermia may be a pulsed, modulated FM RF signal, or a pulse fixed frequency signal. A pulsed signal may permit a relatively higher peak-power level (e.g., a single "burst" pulse at 1000 Watts or more, or a 1000 Watt signal having a duty cycle of about 10% to about 25%)

and may create higher local temperatures at RF absorption enhancer particles (i.e., higher than about 43° C.) without also raising the temperature that high and causing detrimental effects to surrounding cells (for targeted enhancers) or surrounding areas (for general enhancers).

Several systems can be used to remotely determine temperature within a body using sensors or using radiographic means with infrared thermography and thermal MRI. Such remotely determined temperature may be used as feedback to control the power of the signal being delivered to generate hyperthermia. For example, a temperature remotely measured can be used as an input signal for a controller (e.g., a PID controller or a proportional controller or a proportional-integral controller) to control the power of the hyperthermia-generating signal to maintain the generated temperature at a specific temperature setpoint, e.g., 43° C.

Similarly, the location of certain radioisotopes can be remotely determined using radiographic means for imaging of radioimmunotherapy. Accordingly, in any of the embodiments discussed herein, RF absorption enhancers may have substances (such as certain radioisotopes, quantum dots, colored dyes, fluorescent dyes, etc.) added or attached thereto that, when introduced with the RF absorption enhancers, can be used to remotely determine the location of RF absorption enhancers, i.e., the location of the substances can be determined and the location of RF absorption enhancers can be inferred therefrom. In the alternative, these substances can be introduced before or after RF absorption enhancers are introduced and used to remotely determine the location of the RF absorption enhancers. Examples of radioisotopes the location of which can be monitored in a body (e.g., with CT scanners, PET scanners, and other systems capable of detecting particles emitted by such substances) include: technetium 99m, radiogallium, 2FDG (18-F-2-deoxyglucose or 18-F-2-fluorodeoxyglucose) (for PET scans), iodine-131, positron-emitting Iodine 124, copper-67, copper-64, lutetium-177, bismuth-213, rhenium-186, actinium-225, In-111, iodine-123, iodine-131, any one or more of which may be added to RF absorption enhancers. Some of these, e.g., technetium 99m, radiogallium, 2FDG, iodine-131, copper-67, copper-64, lutetium-177, bismuth-213, rhenium-186, actinium-225, and In-111 may also absorb a significant amount of RF energy and therefore function as RF absorption enhancing particles, absorbing RF energy sufficient to raise the temperature of target cells or a target area to a desired temperature level and permitting remote location determination. Such determined location can be used to provide feedback of the location of general or targeted RF absorption enhancers to know which regions of an area or body will be heated by a hyperthermia generating RF signal. For example, the location of these particles (and by inference the location of targeted RF absorption enhancers) can be periodically determined, i.e., monitored, and the hyperthermia generating RF signal applied when enough of the targeted RF absorption enhancers are in a desired location. As another example, the location of these particles (and by inference the location of general or targeted RF absorption enhancers) can be periodically determined, i.e., monitored, and the hyperthermia generating RF signal ceased when the RF absorption enhancers have diffused too much or have moved from a predetermined location. Thus, the location of RF absorption enhancers may be determined via PET scanners, CT scanners, X-ray devices, mass spectroscopy or specialized CT scanners (e.g., Phillips Brilliance CT), and/or infrared, near infrared, thermal MRIs and other optical and/or thermal scanners. For PET scans, exemplary known imaging/treatment substances include: (a) antibodies (or targeting peptides) linked to PET radiometals linked to a cytoxic agent and (b) antibodies (or targeting peptides) linked to PET radiometals linked to beta emitting radionucleotides. In accordance with the teachings herein, one or more RF absorbing particles may be added to these substances (or in the alternative one or more RF absorbing particles may replace either the cytoxic agent or the beta emitting radionucleotides) for combined PET imaging with RF generated hyperthermia. Thus, these phage display antibodies attached to PET radiometals may also be attached to any one or more of the RF absorbing particles discussed herein. This combination of imaging and RF hyperthermia therapy may be accomplished with PET, infrared, near infrared, and MRI.

Imaging techniques can be used to guide the injection (or other introduction) of RF absorption enhancers into a tumor, e.g., a tumor or a portion of a tumor. After injection, a hyperthermia generating RF signal is applied to the target area and thermal imaging can be used to monitor the heat being generated by the RF signal and perhaps directly control the power of the RF signal. Thereafter, follow-up 3-D imaging using traditional methods can be used to determine the results of the hyperthermia. Additionally, imaging combinations are contemplated for imaging of RF absorption enhancers, e.g., using thermal imaging, colored dyes, quantum dots.

Several substances have been described as being injected into a patient, e.g., general RF absorption enhancers, targeted RF absorption enhancers, radioisotopes for remotely determining temperature, radioisotopes capable of being remotely located, etc. It is expected that some or all of these will be injected using a syringe with a needle. The needle may be removed from the patient after injection and before the RF signal is applied to generate hyperthermia. In the alternative, a needle used to inject one or more of the foregoing may be left in place and used as an RF absorption enhancer, i.e., a needle can be made from any number of selected that will heat in the presence of an RF signal. Thus, an ordinary needle may be used as an RF absorption enhancer. Additionally, a needle can be altered to resonate at a selected frequency of an RF hyperthermia-generating signal, which will cause it to heat faster. For example, the tip of a needle can be modified to include a quarter-wave coil, e.g., at the tip of the needle. For example, at an RF frequency of about 13.56 MHz, about six (6) turns of 22 or 24 gauge wire wrapped around the tip of a needle (and perhaps covered with an electrical insulator, e.g., an enamel coating) may greatly enhance RF absorption at the needle tip, effectively creating a hot spot at the tip of the needle subjected to an RF signal. Additionally, or in the alternative, a needle used to inject one or more RF absorption enhancers may have a temperature sensor at its tip in circuit communication with external circuitry to determine a temperature of a target region. As discussed above, this determined temperature may be used to control the power of the RF signal to maintain a desired temperature of a target region.

Viruses (and liposomes and perhaps other carriers) may also be used to improve receptivity of target cells and target areas to targeted RF absorption enhancers, e.g., by having a virus (and/or liposomes and/or another carrier) carry a gene (or other biomolecule) for production of a protein that would be incorporated on the surface of a target cell, making the target cell more identifiable and easily attached by a targeted RF enhancer. For example, a patient may be infected with a virus by removing the cells from the body, growing and increasing their number in a tissue culture, infecting the cells outside the body (ex-vivo), and then inserting them back into the patient. Or the virus may be introduced directly into the body (in-vivo) or into the tumor. Additionally, a virus with such a targeting gene may also be delivered to a target cell by other means, e.g., liposomes or microinfusion. Once the target cell produces the protein that is incorporated to the surface membrane, a dose of a targeted RF absorption enhancer is introduced into the body and the targeted carrier thereof will target and attach to the new protein on the target cell membrane. After waiting for a significant number of the targeted RF absorption enhancers to attach to the new protein, a hyperthermia generating RF signal is transmitted into the target area and the target cells are given a lethal dose of heat or a dose of heat to augment other therapies.

Figure 2:
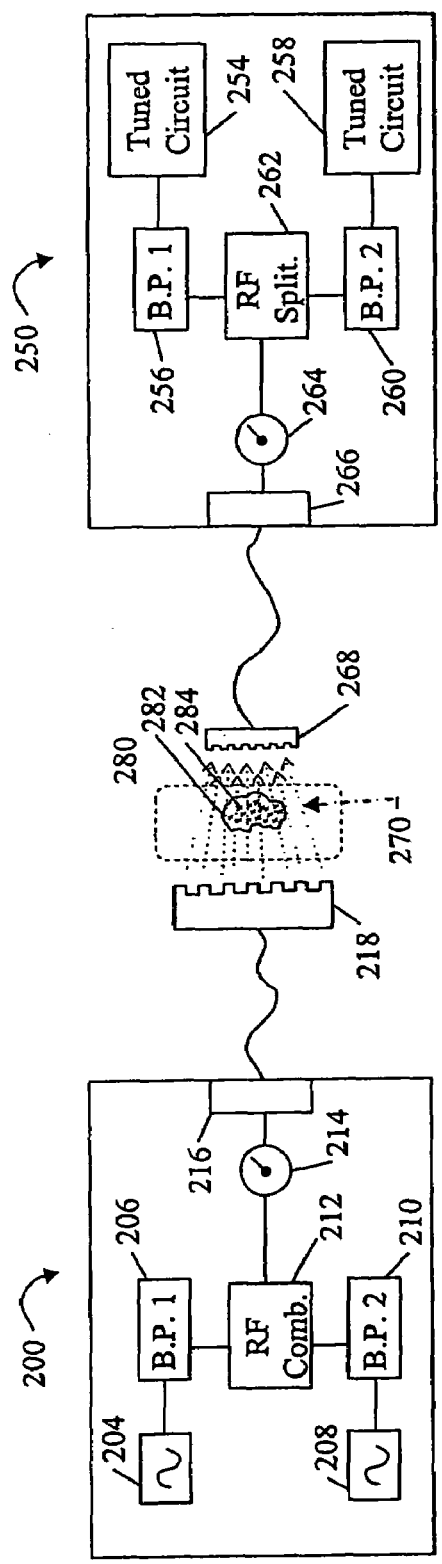
FIG. 2 is an exemplary medium-level block diagram of an RF system for inducing hyperthermia in a target area.

Referring once again to the figures, FIG. 2 illustrates an exemplary embodiment having an RF transmitter 200 in circuit communication with transmission head 218 that transmits an RF signal 270 through a target area 280 to a reception head 268 in circuit communication with an RF receiver 250. The RF transmitter 200 is a multi-frequency transmitter and includes a first RF signal generator 204. The first RF signal generator 204 generates a first signal at a first frequency F1, such as a 16 megahertz frequency. The first RF signal generator 204 is in circuit communications with band pass filter B.P. 1 206, which is in circuit communication with an RF combination circuit 212. Band pass filter B.P. 1 206 is a unidirectional band pass filter that prevents signals at other frequencies from reaching first RF signal generator 204.

RF transmitter 200 includes a second RF signal generator 208. Second RF signal generator 208 generates a second signal at a second frequency F2, such as, for example a 6 megahertz signal. Second signal generator 208 is in circuit communication with band pass filter B.P. 2 210, which is also in circuit communication with the RF combination circuit 212. Band pass filter B.P. 2 210 prevents signals at other frequencies from reaching second RF signal generator 208. Optionally, RF combination circuit 212 includes circuitry to prevent the first and second signals from flowing toward the other signal generators and thus eliminates the need for band pass filter B.P. 1 206 and band pass filter B.P. 2 210.

RF combination circuit 212 combines the first and second signal at frequency F1 and frequency F2 and outputs RF signal 270. Preferably, RF combination circuit 212 is in circuit communication with first meter 214. First meter 214 is used to detect the signal strength of RF signal 270. The RF signal 270 is transmitted via transmission head 218 through the target 280 to reception head 268. Optionally, plug type connectors 216, 266 are provided allowing for easy connection/disconnection of transmission head 218, and reception head 268 respectfully. Reception head 268 is preferably in circuit communications with a second meter 264. Second meter 264 detects the RF signal strength received by the reception head 268. The difference in RF signal strength between first meter 214 and second meter 264 can be used to calculate energy absorbed by the target area 280. Reception head 268 is also in circuit communication with an RF splitter 262. RF splitter 262 separates the RF signal 270 into back into its components, first signal at frequency F1 and second signal at frequency F2. RF splitter 262 is in circuit communication with band pass filter B.P. 1 256, which is in circuit communication with first tuned circuit 254. Similarly, RF splitter 262 is in circuit communication with band pass filter B.P. 2 260, which is in circuit communication with second tuned circuit 258. Optionally, band pass filter B.P. 1, 256 and band pass filter B.P. 2 260 can be replaced with a splitter or powered tee.

First tuned circuit 254 is tuned so that at least a portion of reception head 268 is resonant at frequency F1. Similarly, second tuned circuit 258 is tuned to that at least a portion of reception head 268 is resonant at frequency F2. Since the reception head 268 is resonant at frequencies F1 and F2 the RF signal 270 is forced to pass through the target area 280.

Optionally, an exemplary embodiment having an RF transmitter, similar to that illustrated above, that does not include an RF combination circuit is provided. Instead, the RF transmitter uses a multi-frequency transmission head. In this embodiment, one portion of the transmission head is used to transmit one frequency signal, and a second portion is used to transmit a second frequency signal. In addition, optionally, the reception head and resonant circuits are constructed without the need for a splitter, by providing a reception head having multiple portions wherein the specific portions are tuned to receive specific frequency signals. An example of such a transmission head in more detail illustrated below.

FIG. 2 illustrates another means for concentrating the RF signal on specific target area by using a larger transmission head then reception head. The RF signal 270 transmitted by larger transmission head 218 is received by reception head 268 in such a manner that the RF signal 270 is more concentrated near the reception head 268 than it is near the transmission head 218. The more concentrated the RF signal 270, the higher the amount of energy that can be absorbed by the specific area 282. Thus, positioning the larger transmission head on one side of the target area 280 and positioning the smaller reception head 268 on the other side of and near the specific target area 282 is a means for concentrating the RF signal 270 on the specific target area 282. Optionally, one or more of the tuned circuits 254, 258 in the RF receiver 250 are tuned to have a high quality factor or high "Q." Providing a resonant circuit with a high "Q" allows the tuned head to pick up larger amounts of energy.

FIGS. 3-6 illustrate a number of exemplary transmitter head and reception head configurations. Additionally, the transmitter and receiver heads may be metallic plates. FIG. 3 illustrates a transmitter head 302 having a non-uniform thickness 314. Transmission head 302 is electrically insulated from target area 306 by an insulation layer 308 in contact with the target area. Similarly, reception head 304 is electrically insulated by insulation layer 310. Insulation layer 310 can be in direct contact with target area 306. Insulation layer 308, 310 provide additional means of electrically insulating the transmission head and reception heads from the target area. Reception head 304 also has non-uniform thicknesses 314 and 316. Receiver head 304 is smaller than transmission head 302 and has a smaller cross sectional area on its face. The smaller cross-sectional area of receiver head 304 facilitates in concentrating an RF signal in a specific target area.

FIG. 3A illustrates a face view of the exemplary embodiment of the transmission head 302 of FIG. 3. The transmission head 302 includes a plurality of individual transmission heads 314, 316. Transmission heads 314 provide for transmission of a signal at a first frequency, such as 4 megahertz. Transmission heads 316 provide for transmission of a signal at a second frequency, such as, for example 10 MHz, or 13.56 MHz or any of the lower harmonics of 13.56 MHz mentioned above, e.g., 27.12 MHz. Preferably, the transmission heads 314 and 316 are electrically insulated from one another. In addition, preferable the power output can be controlled to each transmission head, allowing for the power output to be increased or decreased in specific areas based upon the size, shape, or depth of the specific target area. Optionally, all of the transmission heads 314 provide the same power output, and transmission heads 316 provide the same power output.

Obviously the transmission head can contain any number of individual transmission heads. Moreover, the transmission heads can transmit signals at a plurality of frequency, and include, but are not limited to transmission heads that transmit signals at one, two, three, etc. different frequencies. All of which have been contemplated and are within the spirit and scope of the present invention.

FIG. 4 illustrates yet an additional exemplary embodiment. FIG. 4 illustrates transmission head 402 with a wavy surface 412 and reception head 404 having a wavy surface 414. Other useful surface configurations include bumpy, planer, non-uniform, mounded, conical and dimpled surfaces. Varied surface shapes allow for variable depths of heating control. The shape of receiving head 414 is thinner, narrower (not shown) and is selected based upon the size and shape of the specific target area 410 located in the general target area 406.

FIG. 5 illustrates an exemplary embodiment with a non-invasive transmission head 502 and an invasive needle 512. In this embodiment, end of needle 512 is located at least partially within general target area 506 and near specific target area 510. Needle 512 is preferably hollow and has extension members 514 within the needle 512. Once the end of needle 512 is located near the specific target area 510, the extension members 514 are extended and attach to the specific target area 510. Preferably, the specific target area 510 has been targeted with a large concentration of RF absorption enhancers 516. The target area 510, itself, becomes the reception head. The extension members 514 provide circuit communication with the resonant circuit and the target area 510 is resonant at the desired frequency. Providing multiple extension members provides for a more even heating of the specific target area 510. This embodiment allows the RF signal to be concentrated on small areas.

FIG. 6 illustrates yet another exemplary embodiment of transmission and reception heads. In this embodiment, transmission head 602 includes a first transmission head portion 604 and a second transmission head portion 606. The first and second transmission heads 602, 604 are electrically isolated from one another by an insulating member 608. Similarly, reception head 612 includes a first reception portion 614 and a second reception portion 16 that are electrically isolated from one another by an insulation member 618. Providing multiple transmission head portions that are electrically isolated from one another allows the use of multiple frequencies which can be used to heat various shapes and sizes of target areas. Different frequencies can be used to heat thicker and thinner portions of the target area, or deeper target areas allowing for a more uniform heating, or maximum desired heating, of the entire target area. Another exemplary embodiment (not shown) includes a plurality of concentric circles forming transmission head portions and are electrically isolated or insulated from each other.

Figure 7:
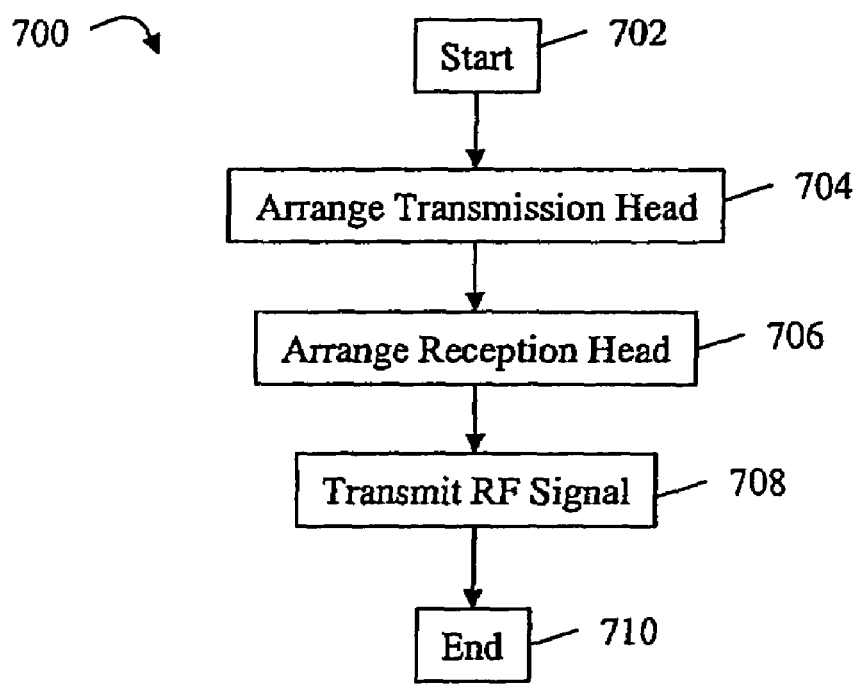
FIG. 7 is an exemplary high-level flowchart of an embodiment of a RF methodology for inducing hyperthermia in a target area.

FIG. 7 illustrates a high level exemplary methodology of for inducing hyperthermia in a target area 700. The methodology begins at block 702. At block 704 the transmission head is arranged. Arrangement of the transmission head is accomplished by, for example, placing the transmission head proximate to and on one side of the target area. At block 706 the reception head is arranged. Arrangement of the reception head is similarly accomplished by, for example, placing the reception head proximate to and on the other side of the target area so that an RF signal transmitted via the transmission head to the reception head will pass through the target area. At block 708 the RF signal is transmitted from the transmission head to the reception head. The RF signal passes through and warms cells in the target area. The methodology ends at block 710 and may be ended after a predetermined time interval and/in response to a determination that a desired heating has been achieved.

Figure 8:
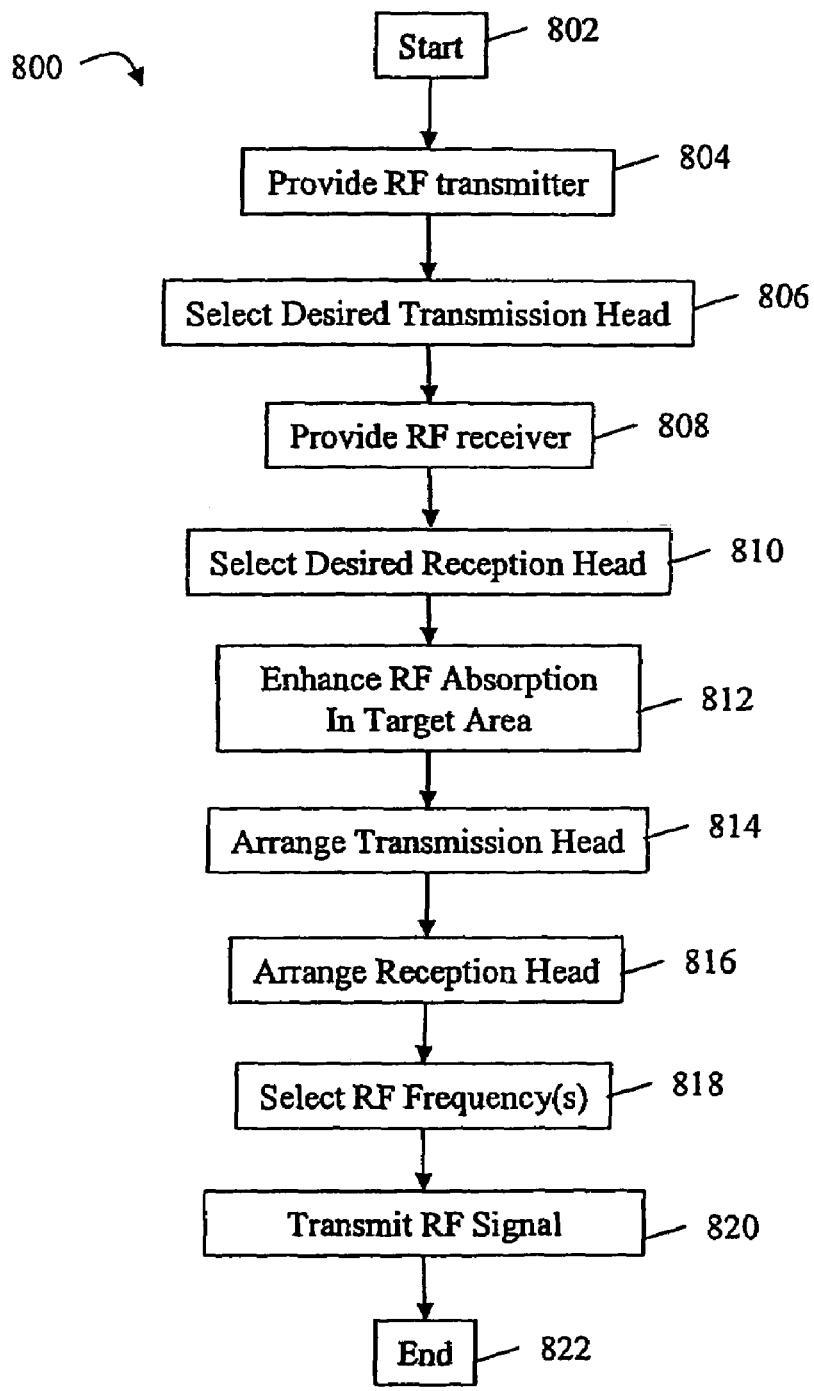
FIG. 8 is an exemplary medium level flow chart of an embodiment of an RF methodology for inducing hyperthermia in a target area.

FIG. 8 illustrates an exemplary methodology for inducing hyperthermia in a target area 800. The methodology begins at block 802. At block 804 an RF transmitter is provided. The RF transmitter may be any type of RF transmitter allowing the RF frequency to be changed or selected. Preferably RF transmitter is a variable frequency RF transmitter. Optionally, the RF transmitter is also multi-frequency transmitter capable of providing multiple-frequency RF signals. Still yet, optionally the RF transmitter is capable of transmitting RF signals with variable amplitudes or pulsed amplitudes.

Preferably, a variety of different shapes and sizes of transmission and reception heads are provided. The transmission head is selected at block 806. The selection of the transmission head may be based in part on the type of RF transmitter provided. Other factors, such as, for example, the depth, size and shape of the general target area, or specific target area to be treated, and the number of frequencies transmitted may also be used in determining the selection of the transmission head.

The RF receiver is provided at block 808. The RF receiver may be tuned to the frequency(s) of the RF transmitter. At block 810, the desired reception head is selected. Similarly to the selection of the transmission head, the reception head is preferably selected to fit the desired characteristics of the particular application. For example, a reception head with a small cross section can be selected to concentrate the RF signal on a specific target area. Various sizes and shapes of the reception heads allow for optimal concentration of the RF signal in the desired target area.

The RF absorption in the target area is enhanced at block 812. The RF absorption rate may be enhanced by, for example, injecting an aqueous solution, and preferably an aqueous solution containing suspended particles of an electrically conductive material. Optionally, the RF absorption in the target area is enhanced by exposing the target cells to one or more targeted RF absorption enhancers, as discussed above.

Arrangement of the transmission head and reception head are performed at blocks 814 and 816 respectfully. The transmission head and reception heads are arranged proximate to and on either side of the target area. The transmission head and reception heads are insulated from the target area. Preferably the heads are insulated from the target area by means of an air gap. Optionally, the heads are insulated from the target area by means of an insulating material. The RF frequency(s) are selected at block 818 and the RF signal is transmitted at block 820. In addition to selecting the desired RF frequency(s) at block 818, preferably, the transmission time or duration is also selected. The duration time is set to, for example, a specified length of time, or set to raise the temperature of at least a portion of the target area to a desired temperature/temperature range, such as, for example to between 106° and 107°, or set to a desired change in temperature. In addition, optionally, other modifications of the RF signal are selected at this time, such as, for example, amplitude, pulsed amplitude, an on/off pulse rate of the RF signal, a variable RF signal where the frequency of the RF signal varies over a set time period or in relation to set temperatures, ranges or changes in temperatures. The methodology ends at block 822 and may be ended after a predetermined time interval and/in response to a determination that a desired heating has been achieved.

Figure 9:
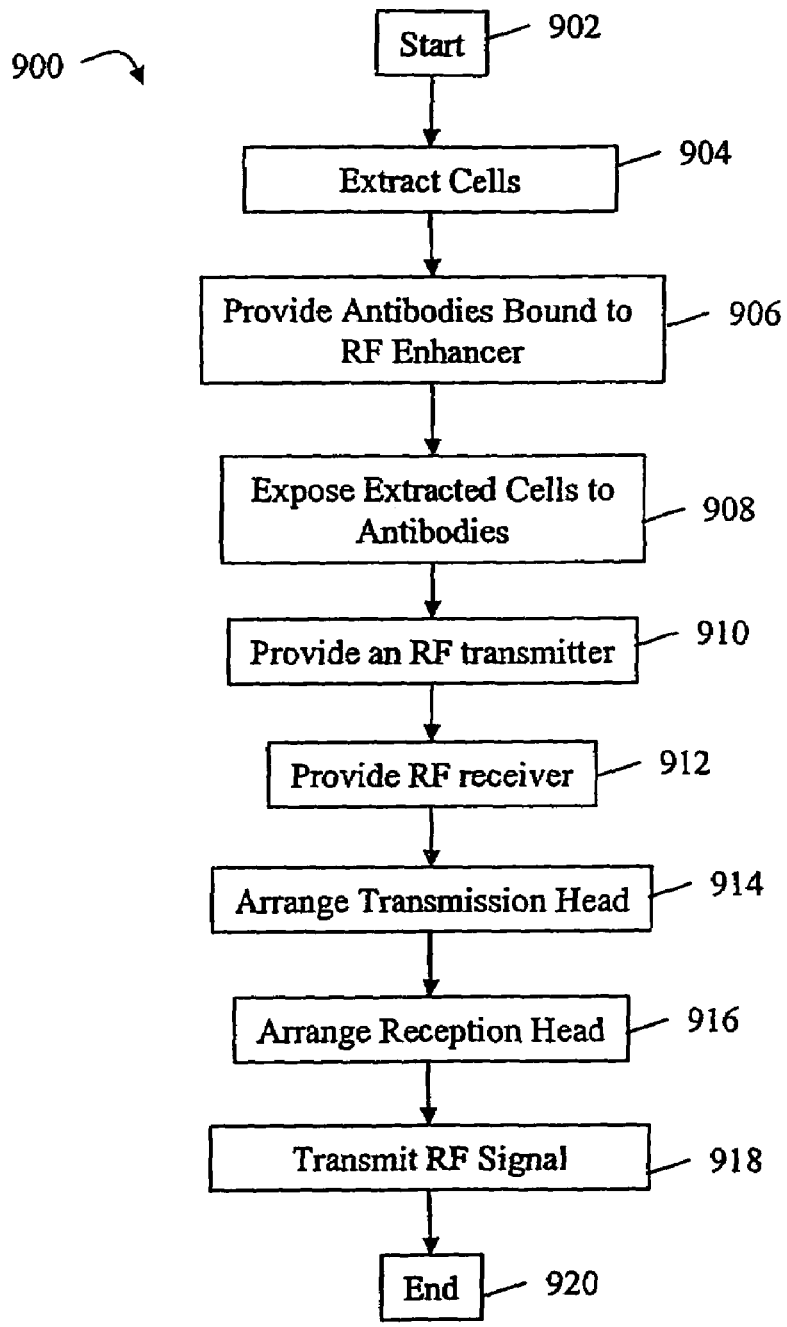
FIG. 9 is an exemplary medium level flow chart of an embodiment of an RF methodology for inducing in-vitro hyperthermia in a target area.

FIG. 9 illustrates an exemplary in-vitro methodology of inducing hyperthermia in target cells 900. The exemplary in-vitro methodology 900 begins at block 902. At block 904, cells to be treated are extracted from a patient and placed in a vessel. The removed cells include at least one or more target cells and are extracted by any method, such as for example, with a needle and syringe. At block 906 antibodies bound with RF enhancers are provided and exposed to the extracted cells. The antibodies bound with RF enhancers attach to one or more of the target cells that are contained within the larger set of extracted cells.

An RF transmitter and RF receiver are provided at blocks 910 and 912 respectively. The transmission head is arranged proximate to and on one side of the target cells in the vessel at block 916. At block 918 the reception head is arranged proximate to and on the other side of the target cells. An RF signal is transmitted at block 918 to increase the temperature of the target cells to, for example, to between 106° and 107°.

Figure 10:
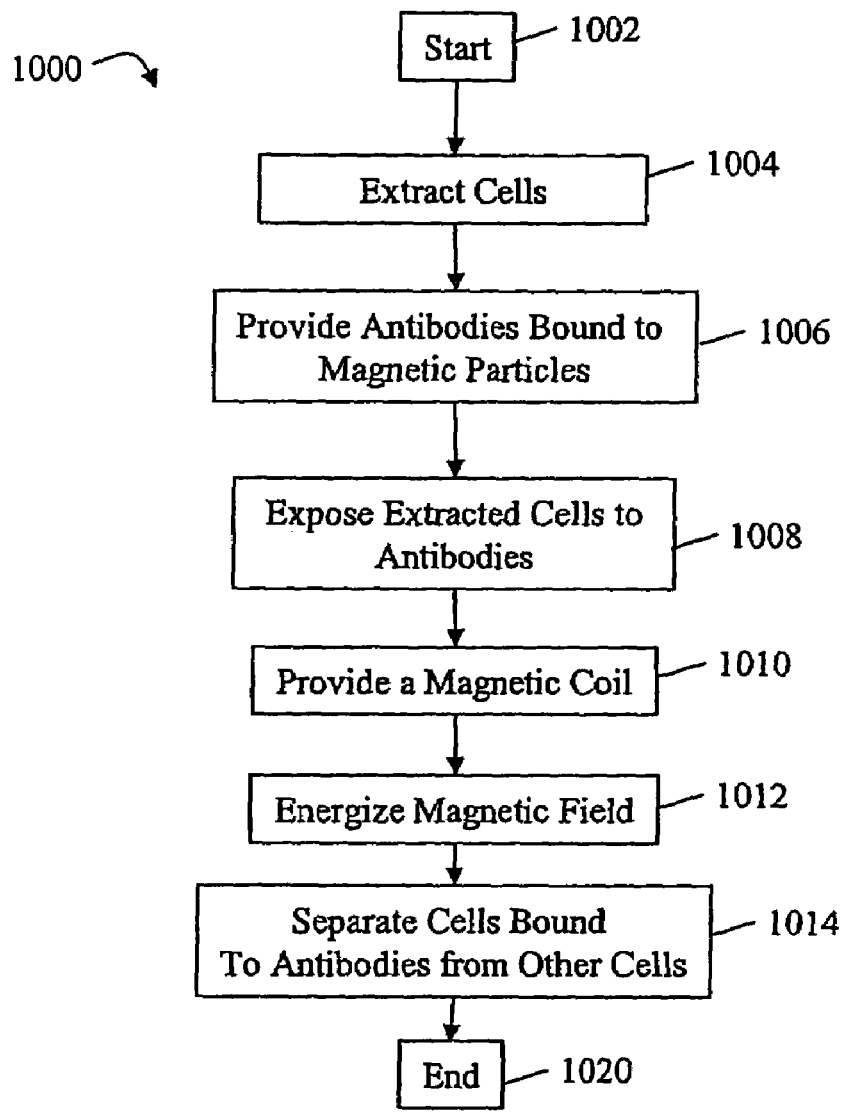
FIG. 10 is an exemplary medium level flow chart of an embodiment of a magnetic methodology for separating cells.

FIG. 10 illustrates an exemplary in-vitro methodology of separating cells 1000. The exemplary in-vitro methodology begins at block 1002. At block 1004, cells to be treated are extracted from a patient and placed in a vessel. The extracted cells include at least one or more target cells and are extracted by any method, such as for example, with a needle and syringe. At block 1006 targeting carriers (with either inherent targeting moieties or targeting moieties attached thereto) bound to magnetic particles (magnetic targeted RF absorption enhancers) are provided and exposed to the extracted cells. The magnetic targeted RF absorption enhancers attach to one or more of the target cells that are contained within the larger set of extracted cells. A magnetic coil is provided at block 1010 and energized at block 1012. The target cells that are bound to the targeting moieties are attracted by the magnetic field. The target cells bound to the targeting moieties are then separated from the other cells. The target cells can be separated by skimming the one or more target cells from the remaining cells, or retaining the one or more target cells in one area of the vessel and removing the other cells. The methodology ends at block 1020 after one or more of the target cells are separated from the other cells.

Figure 11:
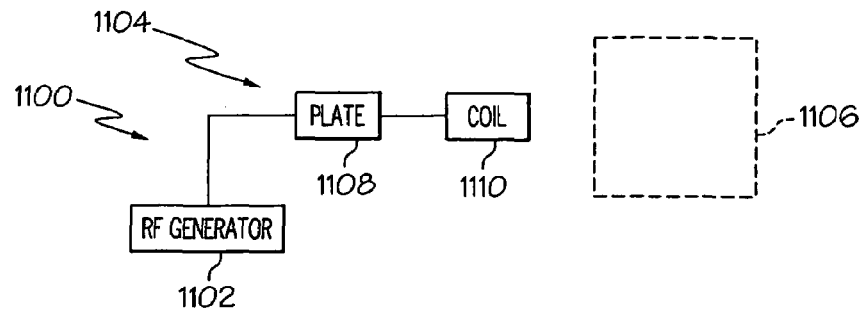
FIGS. 11, 12A, and 12B are high-level schematic block diagrams of exemplary RF systems.

As shown in FIG. 11, an exemplary system 1100 according to the present invention may have an RF generator 1102 transmitting RF energy via a transmission head 1104 toward a target area 1106. The transmission head 1104 may have a plate 1108 operatively coupled to a coil or other inductor 1110. In such a configuration, the head 1104 may itself constitute or be components of a resonant circuit for transmission and/or reception of a hyperthermia-generating RF signal. The plate 1108 may be in circuit communication with the coil or other inductor 1110. The RF generator 1102 may be a commercial transmitter, e.g., the transmitter portion of a YAESU brand FT-1000MP Mark-V transceiver. A hyperthermia generating signal can be generated at about 13.56 MHz (one of the FCC-authorized frequencies for ISM equipment) by the transmitter portion of a YAESU brand FT-1000MP Mark-V transceiver by clipping certain blocking components as known to those skilled in the art. The RF generator 1102 and transmission head 1104 may have associated antenna tuner circuitry (not shown) in circuit communication therewith or integral therewith, e.g., automatic or manual antenna tuner circuitry, to adjust to the impedance of transmission head 1104 and the target area 1106 (and a receiver, if any). The transmitter portion of a YAESU brand FT-1000MP Mark-V transceiver has such integral antenna tuner circuitry (pressing a "Tune" button causes the unit to automatically adjust to the load presented to the RF generator portion). The RF generator 1202 and transmission head may have associated antenna tuner circuitry (not shown) in circuit communication therewith or integral therewith, e.g., automatic or manual antenna tuner circuitry, to adjust to the combined impedance of the target area 1206 and the receiver 1212, 1214 and compensate for changes therein. The transmitter portion of a YAESU brand FT-1000MP Mark-V transceiver has such integral antenna tuner circuitry. Various configurations for the plate 1108 and coil 1110 are possible, as exemplified below. A central axis of the coil, e.g., the central axis of a cylindrical inductor core, may be directed toward the target area.

Figure 12A:
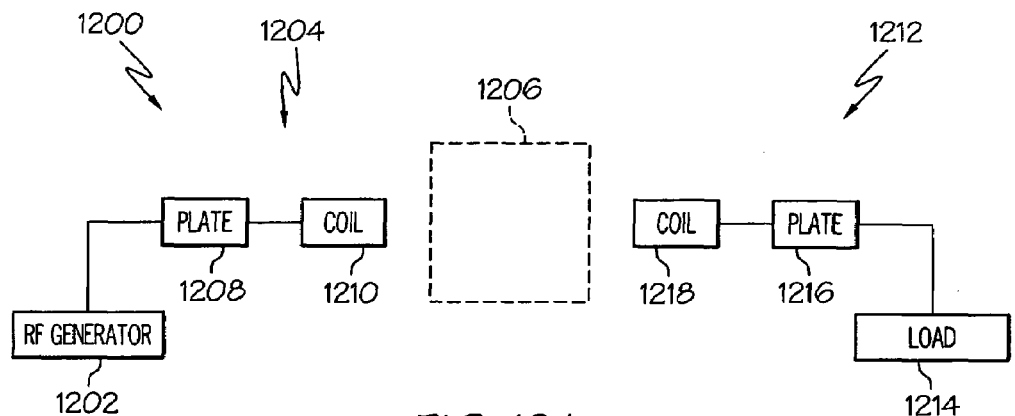

As exemplified by FIG. 12A, an exemplary system 1200 according to the present invention may have an RF generator 1202 transmitting RF energy via a transmission head 1204 (which transmission head 1204 may have a plate 1208 operatively coupled to a coil or other inductor 1210) through a target area 1206 to a reception head 1212 coupled to a load 1214. The reception head 1212 may have a plate 1216 operatively coupled to a coil or other inductor 1218. The RF generator 1202 may be a commercial transmitter, e.g., the transmitter portion of a YAESU brand FT-1000MP Mark-V transceiver, which may be modified as discussed above to generate a 13.56 MHz signal. The RF generator 1202 and transmission head 1204 may have associated antenna tuner circuitry (not shown) in circuit communication therewith or integral therewith, e.g., automatic or manual antenna tuner circuitry, to adjust to the combined impedance of the transmission head 1204, the target area 1206, and the receiver 1212, 1214 and compensate for changes therein. The transmitter portion of a YAESU brand FT-1000MP Mark-V transceiver has such integral antenna tuner circuitry. The load 1214 may be as simple as a non-inductive resistive load (e.g., a grounded power resistor) providing a path for coupled RF energy to dissipate. Various configurations for the plates 1208, 1216 and coils 1210, 1218 are possible, as exemplified below.

Figure 12B:
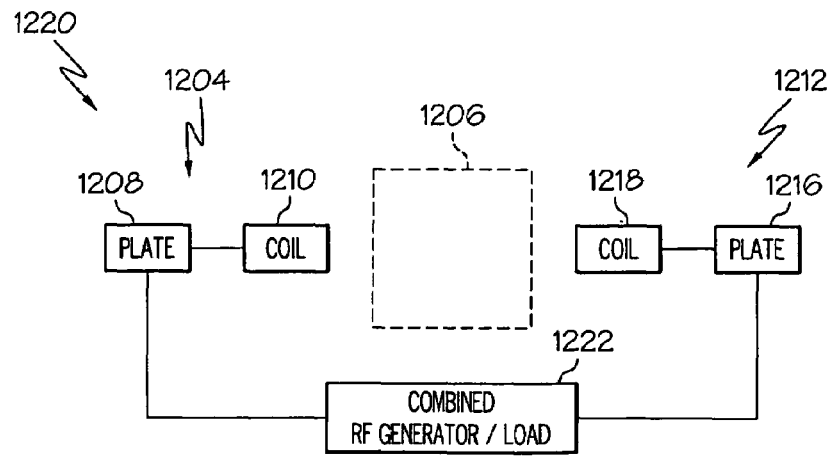

As exemplified by FIG. 12B, an exemplary system 1220 according to the present invention may have a combined RF generator/load 1222 transmitting RF energy via the transmission head 1204 through the target area 1206 to the reception head 1212, which may also be coupled to the combined RF generator/load 1222. The combined RF generator/load 1222 may be a commercial transceiver, e.g., a YAESU brand FT-1000MP Mark-V transceiver, which has built-in automatic antenna tuner circuitry, which can automatically correct for the impedance of the transmission head 1204, the target area 1206, and the reception head 1212. For generating hyperthermia with an RF signal, the YAESU brand FT-1000MP Mark-V transceiver may not generate enough heat, depending on whether RF enhancers are used. Accordingly, the output may need to be amplified with a power amplifier prior to coupling via the transmission head through the target region to the reception head. The configurations of FIGS. 12A and 12B, having a transmission head and a reception head defining a target region therebetween, are favored at the time of the filing of the present application with respect to generating hyperthermia with an RF signal in a target region, e.g., in a tumor or portion of a tumor treated with RF enhancers.

Figure 13:
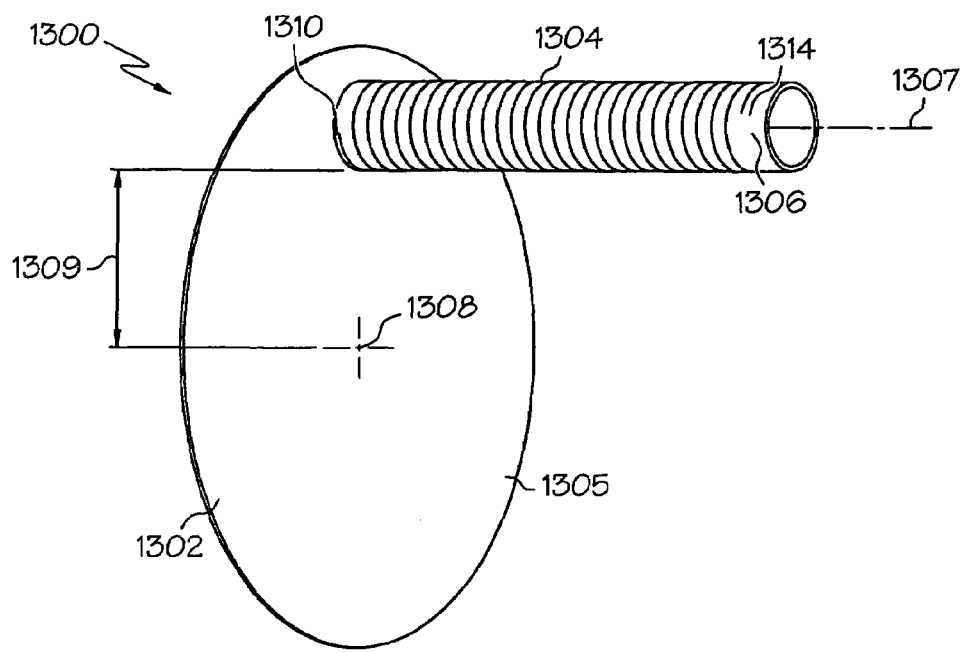
FIG. 13 is a front/left perspective schematic view of another exemplary transmission head.
Figure 14:
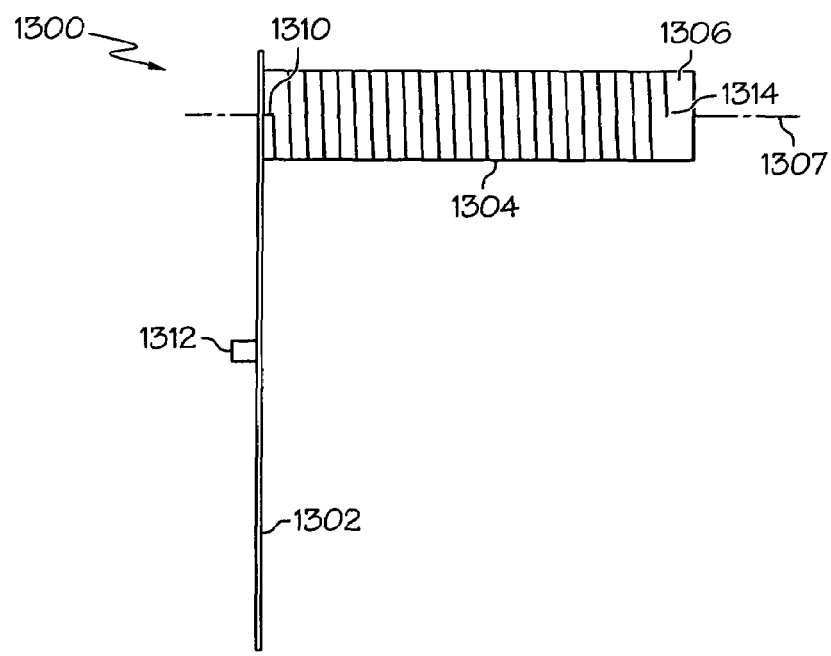
FIG. 14 is a left side schematic view of the exemplary transmission head of FIG. 13.

As shown in FIGS. 13-14, an exemplary head 1300 (as a transmission head and/or as a reception head) may have a plate of conductive material 1302 operatively coupled to a coil or other inductor 1304, an axis of which inductor 1304 may extend generally perpendicular or substantially perpendicular with respect to a surface 1305 of the plate 1302. In such a configuration, the head 1300 may itself constitute or be components of a resonant circuit for transmission and/or reception of a hyperthermia-generating RF signal. The plate of conductive material 1302 may be a generally round plate made of flat, conductive material of substantially uniform thickness. The specific characteristics (surface area, thickness, material, etc.) of the plate 1302 may depend on the specific application and may depend greatly on the frequency or frequencies of electromagnetic radiation directed toward a target area. The plate 1302 may be made from, e.g., copper or silver-plated copper or bronze and should be thick enough to be self-supporting or supported by supporting structures (not shown). The surface area of the plate 1302 may depend on the size of the target area, with a larger plate being used for a larger target area. The surface area of the plate 1302 may depend on the frequency of hyperthermia generating RF signal being used, with lower frequencies, e.g., 13.56 MHz, using a larger plate than higher frequencies, e.g., 27.12 MHz or 40.68 MHz, to help tune to the frequency of hyperthermia generating RF signal being used.

Similarly, the specific characteristics (number of inductors, inductance of each inductor, overall length of each, material for each, material dimensions for each, number of windings for each, coil diameter for each, coil core material for each, etc.) of the inductor 1304 may depend on the specific application and may depend greatly on the frequency or frequencies of electromagnetic radiation directed toward a target area. At higher RF frequencies, (e.g., at about 100 MHz and higher) the inductor 1304 may be a simple straight length of electrical conductor. The inductor 1304 at lower RF frequencies (e.g., about 13.56 MHz) may be configured as a coil 1304 of electrically conductive material, as shown in the figures. If the inductor 1304 is a coil, the coil 1304 may be formed using a core 1306, which may have an axis, e.g., a central axis 1307, that is generally or substantially perpendicular to the surface 1305 of plate 1302. If a plurality of frequencies of electromagnetic radiation are directed toward a target area, a corresponding plurality of electrically insulated inductors may extend generally or substantially perpendicular from the surface 1305 toward the target area. Some or all of the plurality of electrically insulated inductors may be coils, some or all of which may be coaxial or even share a common core 1306. As shown in FIG. 13, the inductor 1304 may be spaced from a central point 1308 (e.g., a center of area or center of mass or axial center) of the plate by a distance 1309. Similarly, the axis 1307 of inductor 1304 may be spaced from the central point 1308 of the plate by a distance (not shown). As shown in FIG. 14, the head 1300 may have an associated electrical connector 1312 for being placed in circuit communication with either an RF generator (in the case of a transmission head) or a load (in the case of a reception head). As discussed below, the plate 1302 may be electrically connected to the inductor 1304 at a point 1310. In the alternative, the plate 1302 may be electrically insulated from the inductor 1304, which may permit the plate to be configured differently from the inductor 1304, e.g., permit the plate 1302 to be grounded or tuned independently of the inductor 1304. Thus, the connector 1312 may be in circuit communication with the plate 1302 and/or the inductor 1304 and the plate 1302 and the inductor 1304 may each have an associated connector. As discussed below, the other end 1314 of coil 1304 may be free or may be connected to a tuning circuit, e.g., a capacitor which may be a variable capacitor.

An exemplary head for use at a frequency of about 13.56 MHz may have a plate formed as an approximately circular shaped disk of flat copper that is about ten (10) inches thick electrically connected to an inductor that is a coil formed from about six (6) turns of 22 or 24 gauge wire would around a 1-inch hollow air core with the windings extending about three (3) inches from the surface of the plate.

Figure 15:
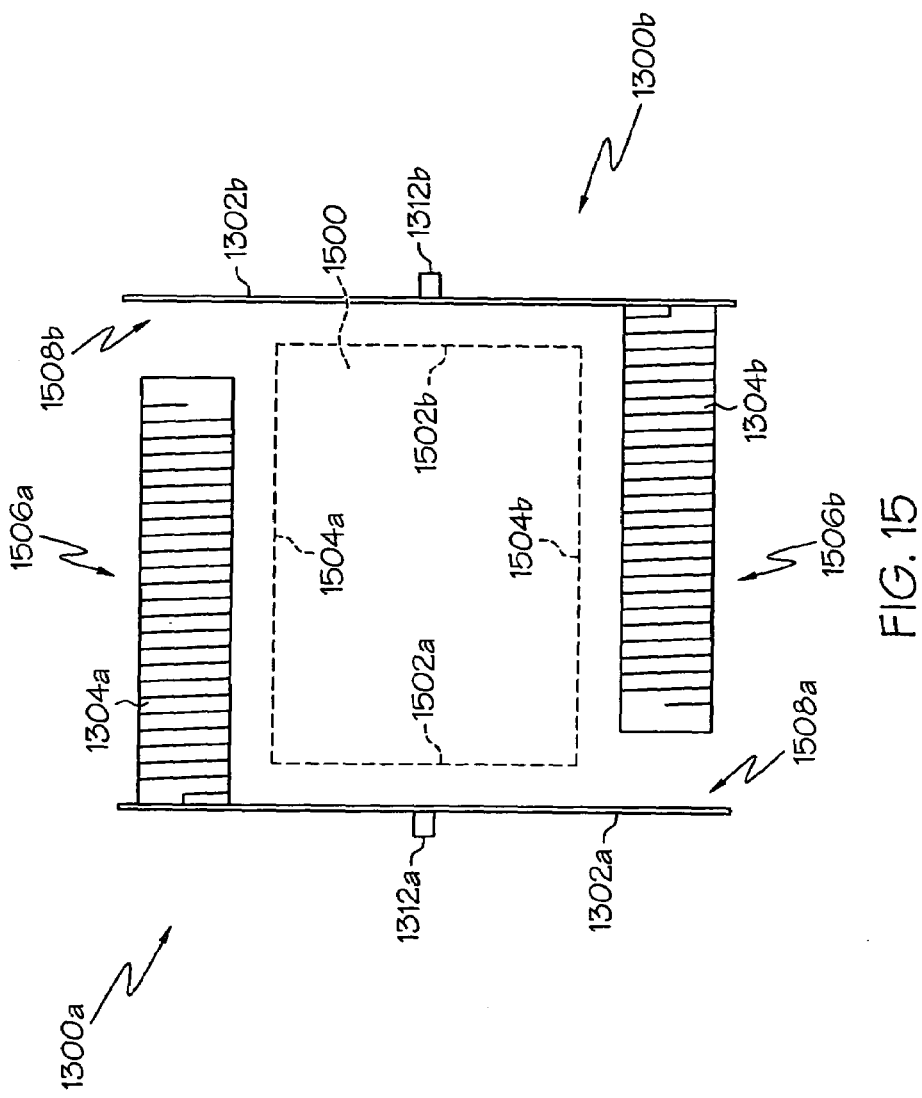
FIG. 15 is a left side schematic view of an exemplary pair of heads of FIG. 13 arranged as an exemplary transmitter head and receiver head.

As shown in FIG. 15, two of the exemplary heads 1300 of FIGS. 13-14 may be used as a transmission head 1300a and reception head 1300b pair. In this configuration, the transmission head 1300a may be in circuit communication with an RF generator via connector 1312a and reception head 1300b may be in circuit communication with a load via connector 1312b with RF electromagnetic energy being coupled from transmission head 1300a to reception head 1300b. As shown in FIG. 15, such a pair may be oriented to create an area 1500 bounded on different sides by the plates 1302a, 1302b and coils 1304a, 1304b. More specifically, the transmission head 1300a and reception head 1300b may be oriented with their plates 1302a, 1302b generally facing each other and their inductors spaced from each other and with their axes extending generally parallel to each other to create area 1500. Area 1500 thus is bounded by a side 1502a proximate plate 1302a, a side 1502b proximate plate 1302b, a side 1504a proximate inductor 1304a, and a side 1504b proximate inductor 1304b. Notice that in this configuration, the distal ends 1502a, 1502b of the inductors 1304a, 1304b are proximate an opposite location 1508b, 1508a of the opposite plate 1302b, 1302a, respectively, which creates an overlap of the inductors 1304a, 1304b that helps form the area 1500. It is expected that RF electromagnetic energy will be coupled from inductor 1304a to inductor 1304b in this side to side configuration. Similarly, it is also believed that RF electromagnetic energy will be coupled from plate 1302a to plate 1302b. Surprisingly, a pair of heads 1300a, 1300b tuned to substantially the same frequency (or harmonics thereof) can be arranged in a skewed configuration (with the plates not directly facing each other and the axes of the coils skewed) and separated by several feet of separation and still permit coupling of significant RF electromagnetic energy from head 1300a to head 1300b.

Figure 16:
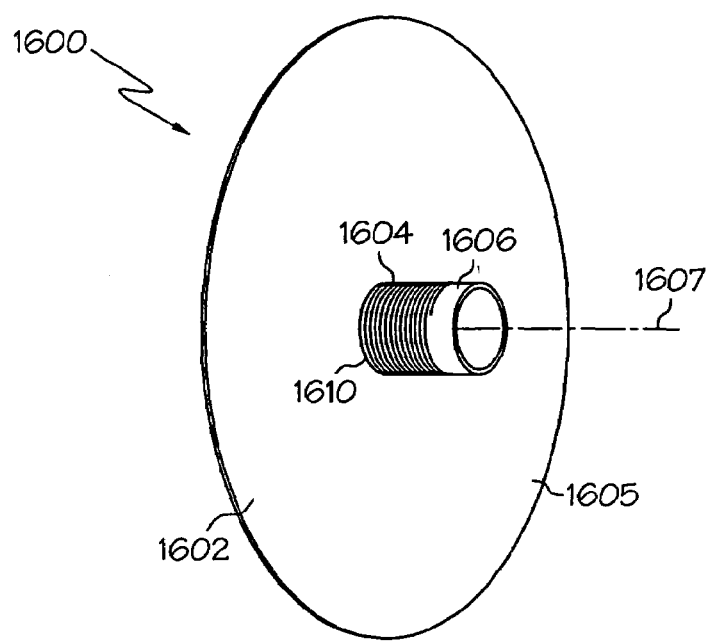
FIG. 16 is a front/left perspective schematic view of yet another exemplary transmission head.
Figure 17:
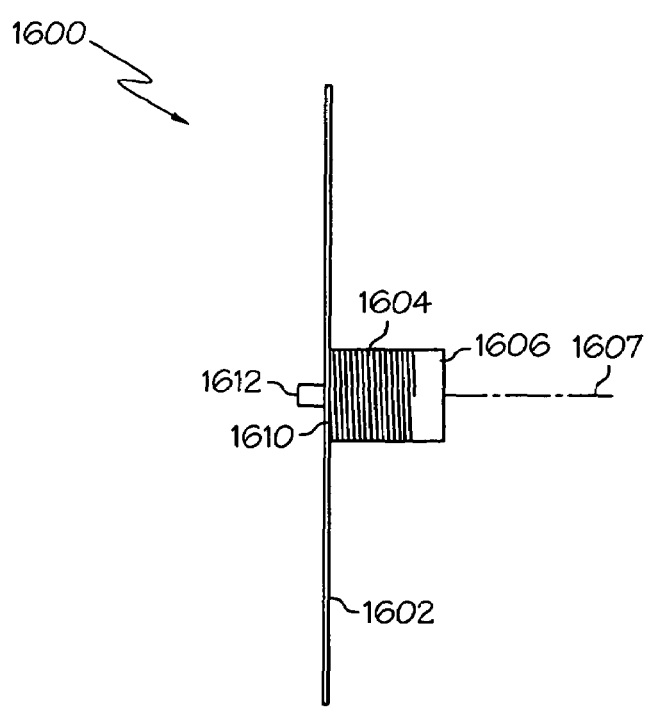
FIG. 17 is a left side schematic view of the exemplary transmission head of FIG. 16.

Another exemplary head configuration is shown in FIGS. 16-17, which shows exemplary head 1600 (as a transmission head and/or as a reception head). The head 1600 is similar in many ways to the head 1300 of FIGS. 13-14. Like head 1300, head 1600 may have a plate of conductive material 1602 operatively coupled to a coil or other inductor 1604, an axis of which inductor 1604 may extend generally perpendicular or substantially perpendicular with respect to a surface 1605 of the plate 1602. In such a configuration, the head 1300 may itself constitute or be components of a resonant circuit for transmission and/or reception of a hyperthermia-generating RF signal. Except as set forth below, all of the discussion above with respect to head 1300 also applies to the head 1600. If the inductor 1604 is a coil, the coil 1604 may be formed using a core 1606, which may have an axis, e.g., a central axis 1607, that is generally or substantially perpendicular to surface 1605 of plate 1602. Unlike head 1300, in head 1600, the axis 1607 of inductor 1604 is shown as being coaxial with a central point of the plate. Also note that the head 1600 has a coil 1604 that has more closely spaced coil windings than coil 1304 of head 1300, which permits coil 1604 to be shown as being shorter than coil 1304 in FIG. 13. As shown in FIG. 17, the head 1600 may have an associated electrical connector 1612 for being placed in circuit communication with either an RF generator (in the case of a transmission head) or a load (in the case of a reception head) with RF electromagnetic energy being coupled from transmission head 1300a to reception head 1300b. As discussed below, the plate 1602 may be electrically connected to the inductor 1604 at a point 1610. In the alternative, the plate 1602 may be electrically insulated from the inductor 1604, which may permit the plate to be configured differently from the inductor 1604, e.g., permit the plate 1602 to be grounded or tuned independently of the inductor 1604. Thus, the connector 1612 may be in circuit communication with the plate 1602 and/or the inductor 1604 and the plate 1602 and the inductor 1604 may each have an associated connector. As discussed below, the other end 1614 of coil 1604 may be free or may be connected to a tuning circuit, e.g., a capacitor which may be a variable capacitor. Again, except as noted above, all of the discussion above with respect to head 1300 also applies to the head 1600.

Figure 18:
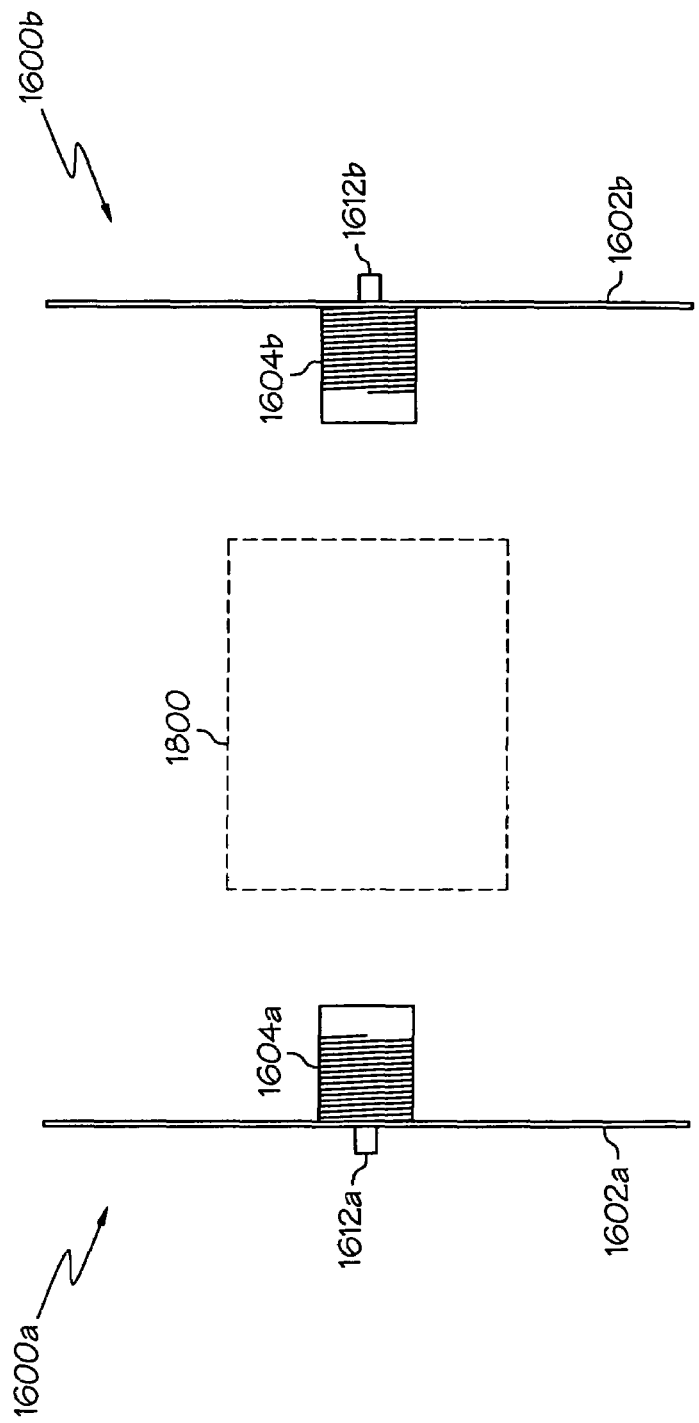
FIG. 18 is a left side schematic view of an exemplary pair of heads of FIG. 16 arranged as an exemplary transmitter head and receiver head.

A pair of the exemplary heads 1600 of FIGS. 16-17 may be used as a transmission head 1600a and reception head 1300b pair, with the transmission head 1600a in circuit communication with an RF generator via connector 1612a and the reception head 1600b in circuit communication with a load via connector 1612b, with RF electromagnetic energy being coupled from transmission head 1600a to reception head 1600b. In such a configuration, the head 1600 may itself constitute or be components of a resonant circuit for transmission and/or reception of a hyperthermia-generating RF signal. Although a pair of heads 1600 may be arranged similar to as shown in FIG. 15, with a pair of inductors side to side and plates facing each other, head 1600 does not really lend itself to this configuration because inductor 1604 is significantly shorter than inductor 1304 and if put in this configuration, there would be a substantially smaller target area and significant portions of the opposite plates not directly facing each other. The head 1600 does lend itself to the configuration shown in FIG. 18 in which a pair of heads 1600a, 1600b are arranged in an "end-fired" configuration, i.e., the coils 1604a, 1604b are coaxial so that the ends of the coils are essentially aimed at each other. In the configuration of FIG. 18, the plates 1602a, 1602b face each other directly. RF electromagnetic energy is coupled from transmission head 1300a to reception head 1300b through an area 1800 between the heads 1600a, 1600b as discussed in more detail below. The central axis of the coils 1604a, 1604b, e.g., the central axis of a cylindrical inductor core, may be directed toward the target area.

Figure 19:
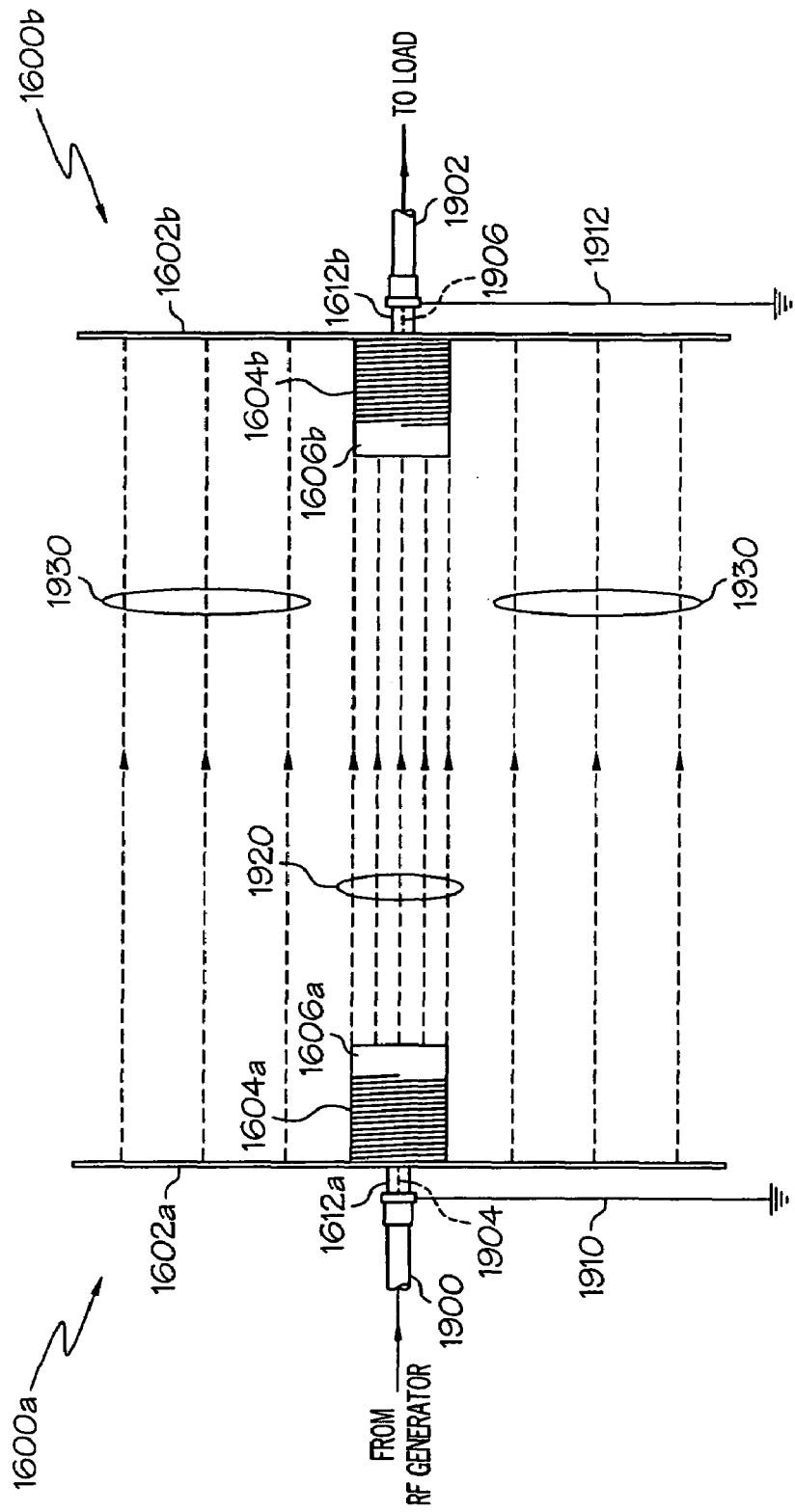
FIGS. 19, 20, 21A, 21B, 22A, and 22B are schematic diagrams showing various exemplary configurations of transmitter heads and receiver heads.

FIG. 19 shows two heads 1600a, 1600b in the "end-fired" configuration of FIG. 18 with transmission head 1600a being in circuit communication with an RF generator via coaxial cable 1900 connected to connector 1312a and the reception head 1300b being in circuit communication with a load via a coaxial cable 1902 connected to connector 1312b, with RF electromagnetic energy being coupled from transmission head 1600a to reception head 1600b. A conductor 1904 within connector 1612a is in circuit communication with plate 1602a and coil 1604a. Similarly, a conductor 1906 within connector 1612b is in circuit communication with plate 1602b and coil 1604b. The shield layer of coaxial cables 1900, 1902 are grounded as shown schematically at 1910, 1912. It is believed that there is significant coupling of RF electromagnetic energy directly between the end-fired inductors 1604a, 1604b, as indicated schematically by the relatively closely spaced rays at 1920. It is also believed that there is additional coupling of RF electromagnetic energy between the plates 1602a, 1602b, although not at as significant a rate, as indicated schematically by the more widely spaced rays at 1930. Again, surprisingly, a pair of such heads 1600a, 1600b tuned to substantially the same frequency (or harmonics thereof) can be arranged in a skewed configuration (with the plates not directly facing each other and the axes of the coils skewed) and separated by several feet of separation and still permit coupling of significant RF electromagnetic energy from head 1600a to head 1600b.

Figure 20:
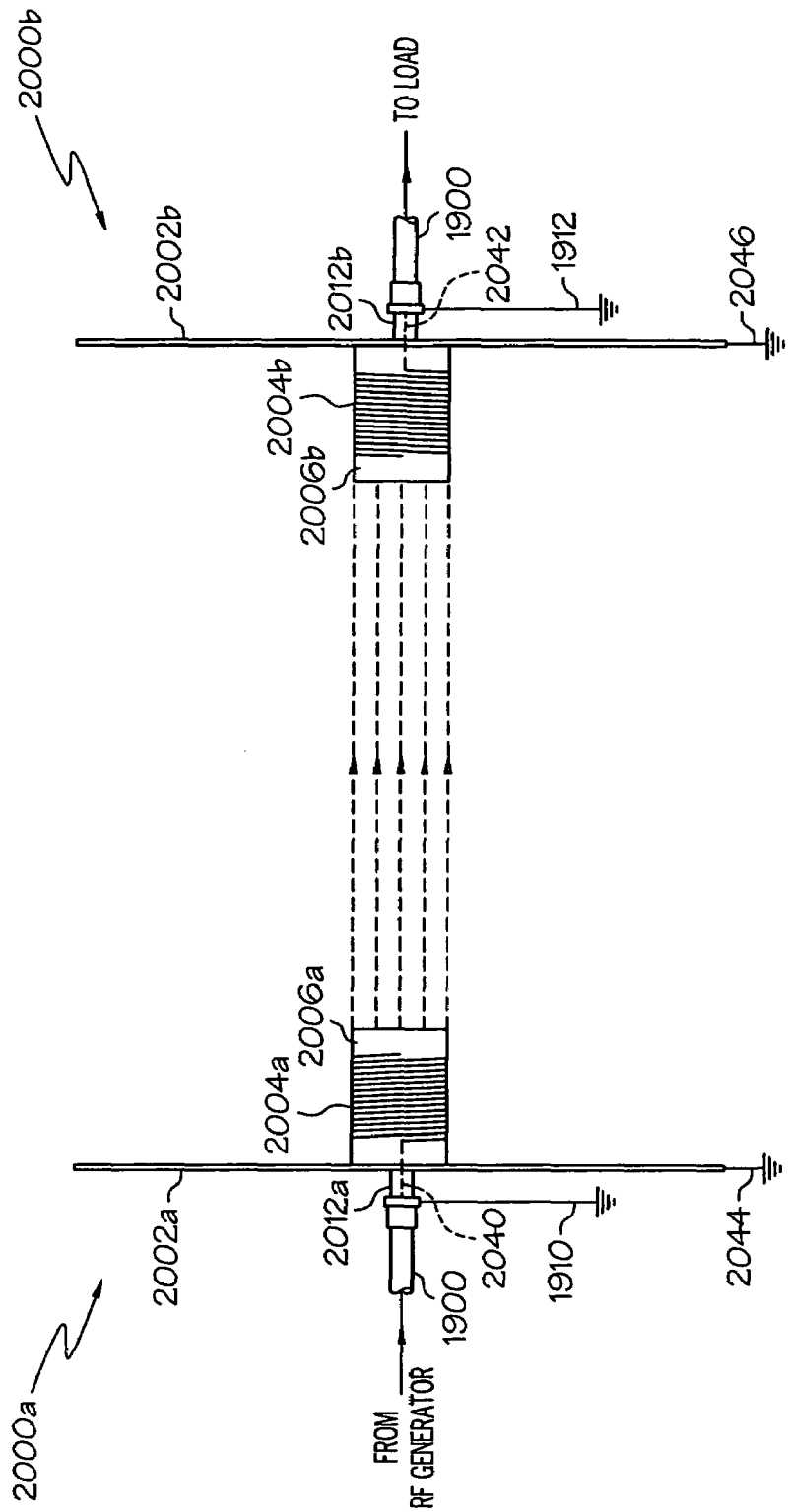

FIG. 20 shows two heads 2000a, 2000b the same as the two heads 1600a, 1600b in the "end-fired" configuration of FIGS. 18 and 19, except that the heads 2000a, 2000b have plates 2002a, 2002b that are electrically insulated from inductors 2004a, 2004b and are grounded. Thus, in the configuration of FIG. 20, the inductor 2004a is in circuit communication with an RF generator via coaxial cable 1900 connected to connector 2012a and inductor 2004b is in circuit communication with a load via a coaxial cable 1902 connected to connector 2012b, with RF electromagnetic energy being coupled from inductor 2004a to inductor 2004b. A conductor 2040 within connector 2012a is in circuit communication with 2004a. Similarly, a conductor 2042 within connector 2012b is in circuit communication with coil 2004b. The shield layer of coaxial cables 1900, 1902 are grounded as shown schematically at 1910, 1912. Additionally, in this configuration, the plates 2002a, 2002b are grounded as shown schematically at 2044, 2046. It is believed that there is significant coupling of RF electromagnetic energy directly between the end-fired inductors 2004a, 2004b, as indicated schematically by the relatively closely spaced rays at 2020.

Figure 21A:
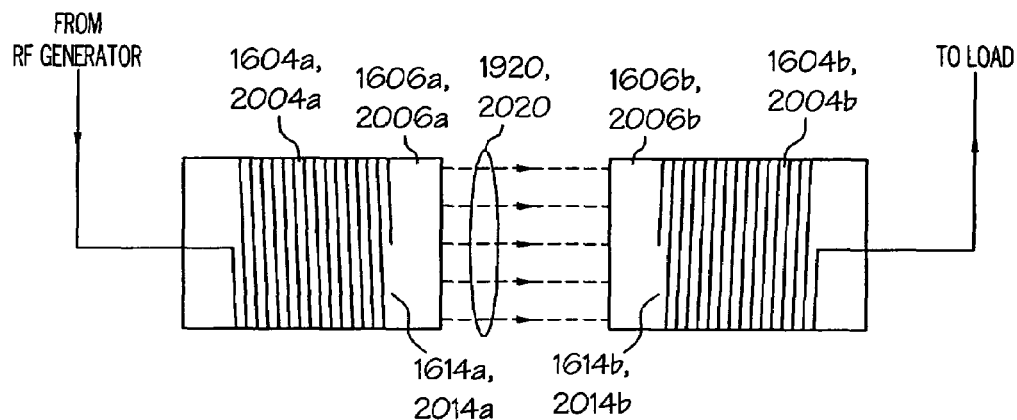
Figure 21B:
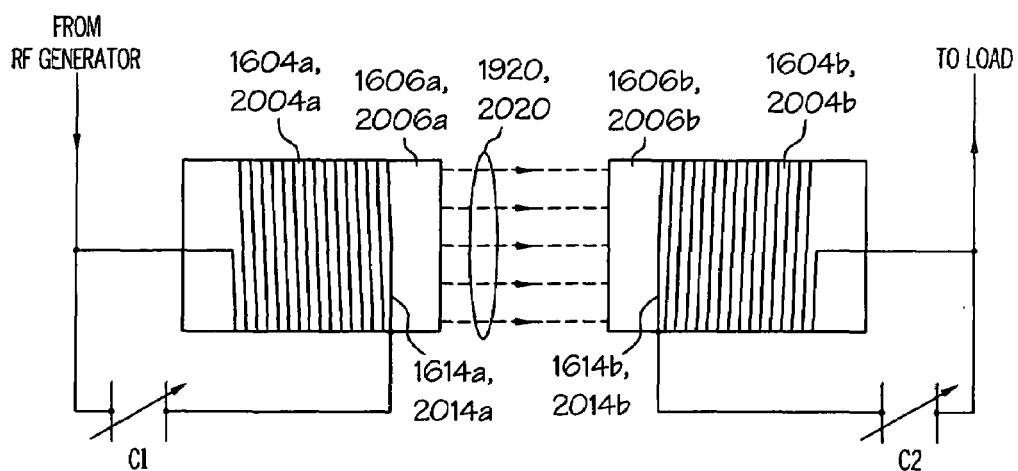
Figure 22A:
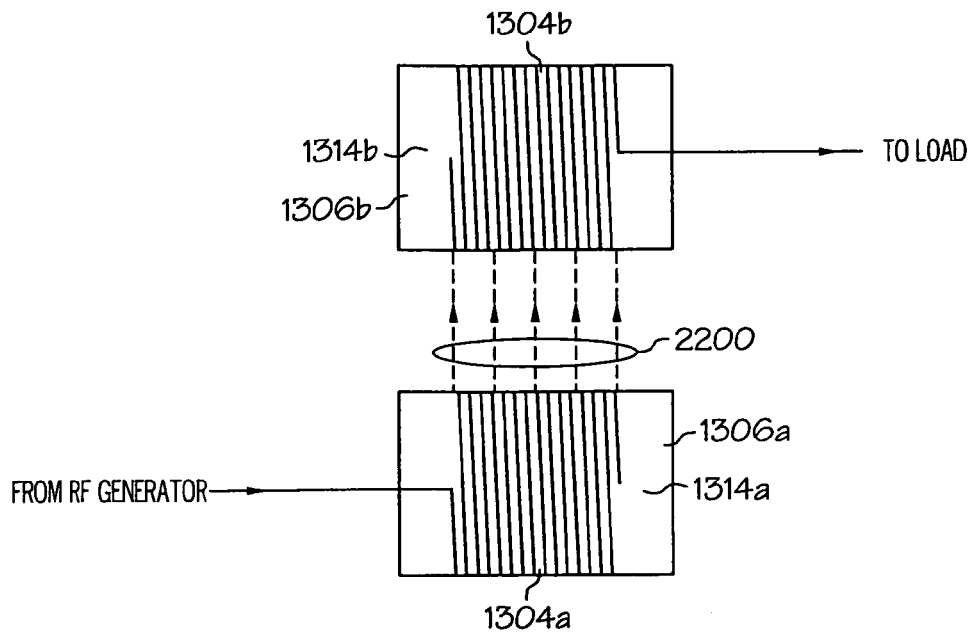
Figure 22B:
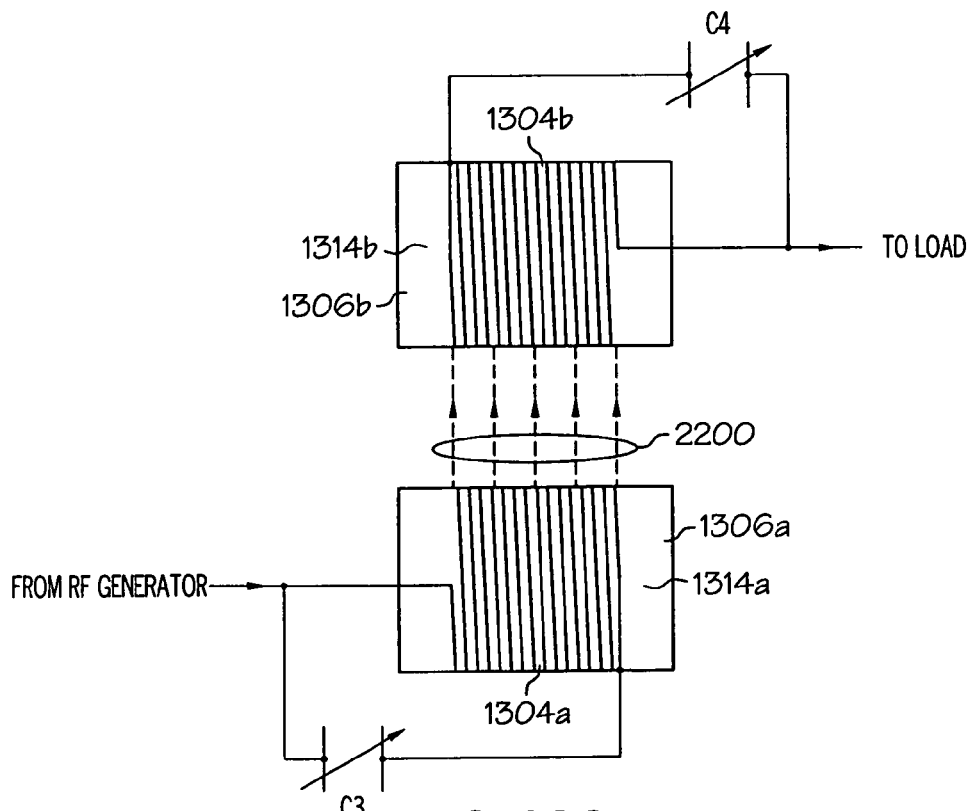

FIGS. 21A and 21B show schematically the end-fired coils 1604a, 1604b, 2004a, 2004b shown in FIGS. 18-20 coupling electromagnetic radiation 1920, 2020 from coil 1604a, 2004a to coil 1604b, 2004b. In FIG. 21A, the distal ends 1614a, 1614b, 2014a, 2014b of coils 1604a, 2004a, 1604b, 2004b are shown as being free. In the alternative, either or both of the distal ends 1614a, 2014a, 1614b, 2014b may be connected to active or passive circuitry to assist in coupling electromagnetic radiation 1920, 2020 from coil 1604a, 2004a to coil 1604b, 2004b, whether there is an associated plate 1602, 2002 or not. For example, either or both of the distal ends 1614a, 2014a, 1614b, 2014b of coils 1604a, 2004a, 1604b, 2004b may be in circuit communication with parallel capacitors C1, C2 as shown in FIG. 21B to assist in coupling electromagnetic radiation from coil to coil. Similarly, FIGS. 22A and 22B show schematically the side to side coils 1304a, 1304b shown in FIG. 15 coupling electromagnetic radiation 2200 from coil 1304a to coil 1304b. In FIG. 22A, the distal ends 1314a, 1314b of coils 1304a, 1304b are shown as being free. In the alternative, either or both of the distal ends 1614a, 1614b may be connected to active or passive circuitry to assist in coupling electromagnetic radiation 2200 from coil 1304a to coil 1304b, whether there is an associated plate 1302 or not. For example, either or both of the distal ends 1314a, 1314b, of coils 1604a, 1604b may be in circuit communication with parallel capacitors C3, C4 as shown in FIG. 22B to assist in coupling electromagnetic radiation from coil to coil. Side to side coils 1304a, 1304b without corresponding plates may be placed in a grounded cage, e.g., a Faraday cage such as a grounded bronze screen box, to prevent re-radiation away from each other, such as re-radiation along their central axes. The use of ungrounded plates in circuit communication with coils (e.g., FIGS. 13-19) tends to confine the RF energy between the plates, which might avoid the need for a Faraday shield. For example, for a pair of the exemplary heads described above (13.56 MHz; plates formed as an approximately circular shaped disk of flat copper that is about ten (10) inches thick electrically connected to a coil formed from about six (6) turns of 22 or 24 gauge wire would around a 1-inch hollow air core with the windings extending about three (3) inches from the surface of the plate) arranged in the configuration of FIG. 18 and tuned to the frequency being transmitted, with the plates spaced about 6" apart, transmitted RF seems to stay substantially within the confines of the plates using a neon bulb, as basic testing has indicated.

Any of the foregoing heads may be used for transmission and/or reception of a hyperthermia-generating RF signal.

Figure 23:
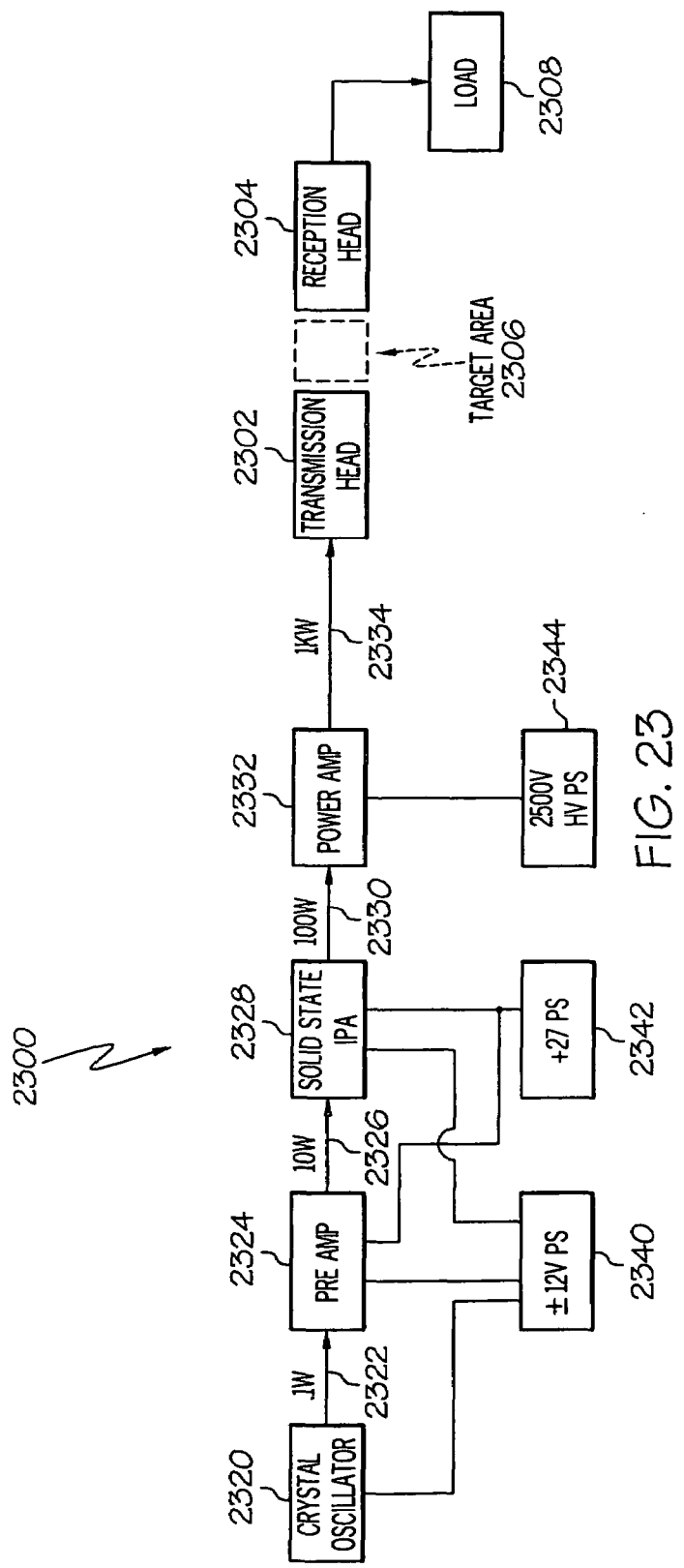
FIG. 23 is a medium-level schematic block diagram of an exemplary RF generator.

FIG. 23 shows an exemplary RF generator 2300 in circuit communication with a transmission head 2302 coupling hyperthermia generating RF energy to a reception head 2304 through a target area 2306. The spacing between the transmission head 2302 and the reception head 2304 preferably, but not necessarily, may be adjusted to accommodate targets of different sizes. The transmission head 2302 and/or the reception head 2304 may have circuitry to accommodate differences in impedance between the transmission head 2302 and the reception head 2304 caused, e.g., by differences in spacing between the heads 2302, 2304 and/or different targets. Such circuitry may include automatic antenna matching circuitry and/or manually adjustable variable components for antenna matching, e.g., high-voltage, high-power RF variable capacitors. The reception head 2304 may be in circuit communication with a load 2308, which may be as simple as a non-inductive resistive load (e.g., a grounded power resistor) providing a path for coupled RF energy to dissipate. The transmission head 2302 and the reception head 2304 may each be in any of the various head configurations shown and/or described herein. The transmission head 2302 and/or the reception head 2304 may have an associated power meter, which may be used as feedback to adjust any manually adjustable variable components for antenna matching until a substantial amount of power being transmitted by transmission head 2302 is being received by the reception head 2304. In general, such power meters may be separate or integral with the RF generator, and/or the RF receiver, and/or the combined RF generator/receiver. If separate power meters are used, they may be located remotely with the transmission head 2302 and the reception head 2304 to facilitate contemporaneous adjustment and tuning of the transmission head 2302 and the reception head 2304.

The exemplary RF generator 2300 of FIG. 23 comprises a crystal oscillator 2320 that generates a signal 2322 at a power level of about 0.1 Watts at a selectable frequency to a preamplifier 2324. The signal 2322 may be modified before the preamplifier 2324 to have a variable duty cycle, e.g., to provide a pulsed RF signal at a variable duty cycle. As discussed above, it may be beneficial to use a frequency modulated (FM) RF signal to create hyperthermia with certain energy absorption enhancer particles. Accordingly, in addition, or in the alternative, signal 2322 may be modified before the preamplifier 2324 to be an FM signal. For example, pre-amp 2324 may be replaced with an amplifying FM exciter to modulate the signal 2322 with a selected modulation frequency and amplify the signal as pre-amp 2324. The parameters of the FM RF signal used to generate hyperthermia may be selected to correspond to the specific sample of particles being used as energy absorption enhancer particles. The center frequency of an FM hyperthermia generating RF signal may correspond to a resonant frequency of nominally sized particles used as energy absorption enhancer particles and the modulation of the FM hyperthermia generating RF signal may correspond to the size tolerance of the particles used as energy absorption enhancer particles, as discussed above.

The preamplifier 2324 amplifies the RF signal 2322 (or the modified signal 2322) and generates a signal 2326 at a power level of about 10 Watts to an intermediate power amplifier 2328. The intermediate power amplifier 2328 amplifies the RF signal 2326 and generates an RF signal 2330 at a power level of about 100 Watts to a power amplifier 2332. The power amplifier 2332 amplifies the RF signal 2330 and generates a selectable power RF signal 2334 at a selectable power level of 0.00 Watts to about 1000 Watts to the transmission head 2302. A power meter may be placed in circuit communication between the power amplifier 2332 and the transmission head 2302 to measure the RF power to the transmission head 2302. Similarly, a power meter may be placed in circuit communication between the reception head 2304 and the load 2306 to measure the RF power from the reception head 2304. The preamplifier 2324 may be a hybrid preamplifier. The intermediate power amplifier 2328 may be a solid state Class C intermediate power amplifier. The power amplifier 2332 may be a zero-bias grounding grid triode power amplifier, which are relatively unaffected by changes in output impedance, e.g., a 3CX15000A7 power amplifier.

The exemplary RF generator 2300 shown generates a high-power fixed-frequency hyperthermia generating RF signal at an adjustable power range of 0.00 Watts to about 1000 Watts. The exemplary RF generator 2300 shown may be modified to generate high-power fixed-frequency hyperthermia generating RF signals at selected frequencies or at an adjustable frequency, any of which may be pulsed or FM modulated. For example, a plurality of separate crystals, preamplifiers, and IPAs, each at a different frequency, e.g., 13.56 MHz, 27.12 MHz, 40.68 MHz, 54.24 MHz, 67.80 MHz, and 81.36 MHz (not shown) may be switchably connected to the power amplifier 2332 for generation of a high-power hyperthermia generating signal at a frequency selected from a plurality of frequencies.

While the present invention has been illustrated by the description of embodiments thereof, and while the embodiments have been described in some detail, it is not the intention of the applicant to restrict or in any way limit the scope of the appended claims to such detail. Additional advantages and modifications will readily appear to those skilled in the art. For example, any of the transmitter circuits and/or transceiver circuits described herein can be used with virtually any of the RF absorption enhancers (general and/or targeted), described herein, or with any combination or permutation thereof, or without any RF absorption enhancer. As another example, the RF signal (single frequency or FM modulated) may be modulated with another signal, such as, for example, a square wave (e.g. a 300-400 Hz square wave). Modulating the RF signal with a square wave may stimulate the tissue and enhance heating; square waves introduce harmonics that may enhance modulation utilized; and square waves may also be used to pulse the transmitted signal to change the average duty cycle. Another example includes total body induced hyperthermia to treat the patient's entire body. In this example, the transmission and reception heads are as large as the patient and hyperthermia is induced in the entire body. Cooling the blood may be required to prevent overheating and can be accomplished in any manner. Additionally, the steps of methods herein may generally be performed in any order, unless the context dictates that specific steps be performed in a specific order. Therefore, the invention in its broader aspects is not limited to the specific details, representative apparatus and methods, and illustrative examples shown and described. Accordingly, departures may be made from such details without departing from the spirit or scope of the applicant's general inventive concept.

What is claimed is:

1. A method for killing or damaging target cells in a patient, comprising:
   introducing into the patient RF absorption enhancers capable of selectively binding to the target cells and further capable of generating sufficient heat to kill or damage the bound target cells by heat generated solely by the application of an RF field generated by an RF signal between a transmission head and a reception head that is different from the transmission head;
   arranging the transmission and reception heads on opposite sides of a portion of the patient for treatment; and
   irradiating the portion of the patient between the transmission and reception heads containing RF absorption enhancers with an RF field to kill or damage the target cells from the heat generated by the RF absorption enhancers.

2. The method of claim 1, wherein the patient is irradiated with a field consisting essentially of an RF field between the transmission and reception heads.

3. The method of claim 1, wherein the patient is irradiated solely with an RF field between the transmission and reception heads.

4. The method of claim 1, wherein the RF absorption enhancers are excited to generate heat for killing or damaging the target cells by hyperthermia solely by irradiation with a field consisting essentially of an RF field between the transmission and reception heads.

5. The method according to claim 4 wherein the RF absorption enhancers comprise at least one targeting moiety bound to at least one electrically conductive particle.

6. The method according to claim 4 wherein the RF absorption enhancers comprise at least one targeting moiety bound to at least one particle of electrically conductive metal.

7. The method according to claim 4 wherein the RF absorption enhancers comprise at least one targeting moiety bound to at least one nanoparticle of electrically conductive metal.

8. The method according to claim 4 wherein the RF absorption enhancers comprise at least one targeting moiety bound to at least one particle of electrically conductive gold.

9. The method according to claim 4 wherein the RF absorption enhancers comprise at least one targeting moiety bound to at least one nanoparticle of electrically conductive gold.

10. The method according to claim 4 wherein the RF absorption enhancers comprise at least one targeting moiety bound to at least one particle that rectifies the RF signal, the at least one particle being small enough to be carried to a target cell via the patient's vascular system.

11. The method according to claim 4 wherein the RF absorption enhancers comprise at least one targeting moiety bound to at least one tuned electronic circuit small enough to be carried to a target cell via the patient's vascular system, wherein the at least one tuned electronic circuit has at least one particle frequency associated therewith, and further wherein the RF signal has at least one frequency corresponding to the at least one particle frequency.

12. The method according to claim 4 wherein the RF absorption enhancers comprise at least one biomolecule bound to at least one electrically conductive particle.

13. The method according to claim 4 wherein the RF absorption enhancers comprise at least one biomolecule bound to at least one particle of electrically conductive metal.

14. The method according to claim 4 wherein the RF absorption enhancers comprise at least one biomolecule bound to at least one nanoparticle of electrically conductive metal.

15. The method according to claim 4 wherein the RF absorption enhancers comprise at least one biomolecule bound to at least one particle of electrically conductive gold.

16. The method according to claim 4 wherein the RF absorption enhancers comprise at least one biomolecule bound to at least one nanoparticle of electrically conductive gold.

17. The method according to claim 4 wherein the RF absorption enhancers comprise at least one antibody or antibody fragment or other targeting moiety bound to at least one electrically conductive particle.

18. The method according to claim 4 wherein the RF absorption enhancers comprise at least one antibody or antibody fragment or other targeting moiety bound to at least one particle of electrically conductive metal.

19. The method according to claim 4 wherein the RF absorption enhancers comprise at least one antibody or antibody fragment or other targeting moiety bound to at least one nanoparticle of electrically conductive metal.

20. The method according to claim 4 wherein the RF absorption enhancers comprise at least one antibody or antibody fragment or other targeting moiety bound to at least one particle of electrically conductive gold.

21. The method according to claim 4 wherein the RF absorption enhancers comprise at least one antibody or antibody fragment or other targeting moiety bound to at least one nanoparticle of electrically conductive gold.

22. The method according to claim 4 wherein the RF absorption enhancers comprise at least one targeting moiety bound to at least one electrically conductive nanoparticle.

23. The method according to claim 4 wherein the RF absorption enhancers comprise at least one targeting moiety bound to at least one nanoparticle of electrically conductive metal.

24. The method of claim 1, wherein the RF absorption enhancers are excited to generate heat for killing or damaging the target cells by hyperthermia solely by irradiation with an RF field between the transmission and reception heads.

25. The method according to claim 24 wherein the RF absorption enhancers comprise at least one targeting moiety bound to at least one electrically conductive particle.

26. The method according to claim 24 wherein the RF absorption enhancers comprise at least one targeting moiety bound to at least one particle of electrically conductive metal.

27. The method according to claim 24 wherein the RF absorption enhancers comprise at least one targeting moiety bound to at least one nanoparticle of electrically conductive metal.

28. The method according to claim 24 wherein the RF absorption enhancers comprise at least one targeting moiety bound to at least one particle of electrically conductive gold.

29. The method according to claim 24 wherein the RF absorption enhancers comprise at least one targeting moiety bound to at least one nanoparticle of electrically conductive gold.

30. The method according to claim 24 wherein the RF absorption enhancers comprise at least one targeting moiety bound to at least one particle that rectifies the RF signal, the at least one particle being small enough to be carried to a target cell via the patient's vascular system.

31. The method according to claim 24 wherein the RF absorption enhancers comprise at least one targeting moiety bound to at least one tuned electronic circuit small enough to be carried to a target cell via the patient's vascular system, wherein the at least one tuned electronic circuit has at least one particle frequency associated therewith, and further wherein the RF signal has at least one frequency corresponding to the at least one particle frequency.

32. The method according to claim 24 wherein the RF absorption enhancers comprise at least one biomolecule bound to at least one electrically conductive particle.

33. The method according to claim 24 wherein the RF absorption enhancers comprise at least one biomolecule bound to at least one particle of electrically conductive metal.

34. The method according to claim 24 wherein the RF absorption enhancers comprise at least one biomolecule bound to at least one nanoparticle of electrically conductive metal.

35. The method according to claim 24 wherein the RF absorption enhancers comprise at least one biomolecule bound to at least one particle of electrically conductive gold.

36. The method according to claim 24 wherein the RF absorption enhancers comprise at least one biomolecule bound to at least one nanoparticle of electrically conductive gold.

37. The method according to claim 24 wherein the RF absorption enhancers comprise at least one antibody or antibody fragment or other targeting moiety bound to at least one electrically conductive particle.

38. The method according to claim 24 wherein the RF absorption enhancers comprise at least one antibody or antibody fragment or other targeting moiety bound to at least one particle of electrically conductive metal.

39. The method according to claim 24 wherein the RF absorption enhancers comprise at least one antibody or antibody fragment or other targeting moiety bound to at least one nanoparticle of electrically conductive metal.

40. The method according to claim 24 wherein the RF absorption enhancers comprise at least one antibody or antibody fragment or other targeting moiety bound to at least one particle of electrically conductive gold.

41. The method according to claim 24 wherein the RF absorption enhancers comprise at least one antibody or antibody fragment or other targeting moiety bound to at least one nanoparticle of electrically conductive gold.

42. The method according to claim 24 wherein the RF absorption enhancers comprise at least one targeting moiety bound to at least one electrically conductive nanoparticle.

43. The method according to claim 24 wherein the RF absorption enhancers comprise at least one targeting moiety bound to at least one nanoparticle of electrically conductive metal.

44. The method according to claim 1 wherein the RF absorption enhancers comprise at least one targeting moiety bound to at least one electrically conductive particle.

45. The method according to claim 44 wherein the RF absorption enhancers comprise at least one targeting moiety bound directly to at least one electrically conductive particle.

46. The method according to claim 1 wherein the RF absorption enhancers comprise at least one targeting moiety bound to at least one particle of electrically conductive metal.

47. The method according to claim 1 wherein the RF absorption enhancers comprise at least one targeting moiety bound to at least one nanoparticle of electrically conductive metal.

48. The method according to claim 1 wherein the RF absorption enhancers comprise at least one targeting moiety bound to at least one particle of electrically conductive gold.

49. The method according to claim 1 wherein the RF absorption enhancers comprise at least one targeting moiety bound to at least one nanoparticle of electrically conductive gold.

50. The method according to claim 1 wherein the RF absorption enhancers comprise at least one targeting moiety bound to at least one particle that rectifies the RF signal, the at least one particle being small enough to be carried to a target cell via the patient's vascular system.

51. The method according to claim 1 wherein the RF absorption enhancers comprise at least one targeting moiety bound to at least one tuned electronic circuit small enough to be carried to a target cell via the patient's vascular system, wherein the at least one tuned electronic circuit has at least one particle frequency associated therewith, and further wherein the RF signal has at least one frequency corresponding to the at least one particle frequency.

52. The method according to claim 1 wherein the RF absorption enhancers comprise at least one biomolecule bound to at least one electrically conductive particle.

53. The method according to claim 1 wherein the RF absorption enhancers comprise at least one biomolecule bound to at least one particle of electrically conductive metal.

54. The method according to claim 1 wherein the RF absorption enhancers comprise at least one biomolecule bound to at least one nanoparticle of electrically conductive metal.

55. The method according to claim 1 wherein the RF absorption enhancers comprise at least one biomolecule bound to at least one particle of electrically conductive gold.

56. The method according to claim 1 wherein the RF absorption enhancers comprise at least one biomolecule bound to at least one nanoparticle of electrically conductive gold.

57. The method according to claim 1 wherein the RF absorption enhancers comprise at least one antibody or antibody fragment or other targeting moiety bound to at least one electrically conductive particle.

58. The method according to claim 1 wherein the RF absorption enhancers comprise at least one antibody or antibody fragment or other targeting moiety bound to at least one particle of electrically conductive metal.

59. The method according to claim 1 wherein the RF absorption enhancers comprise at least one antibody or antibody fragment or other targeting moiety bound to at least one nanoparticle of electrically conductive metal.

60. The method according to claim 1 wherein the RF absorption enhancers comprise at least one antibody or antibody fragment or other targeting moiety bound to at least one particle of electrically conductive gold.

61. The method according to claim 1 wherein the RF absorption enhancers comprise at least one antibody or antibody fragment or other targeting moiety bound to at least one nanoparticle of electrically conductive gold.

62. The method according to claim 1 wherein the RF absorption enhancers comprise at least one targeting moiety bound to at least one electrically conductive nanoparticle.

63. The method according to claim 1 wherein the RF absorption enhancers comprise at least one targeting moiety bound to at least one nanoparticle of electrically conductive metal.

64. The method according to any of claim 1, claim 44, claim 46, claim 47, claim 48, claim 49, claim 50, claim 62, and claim 63 wherein the heating of the RF absorption enhancers is caused without a separate, external magnetic field to induce heating of the RF absorption enhancers by the RF signal.

65. The method according to any of claims 1-10, 22-24, 44, 46-50, 62 and 63, wherein the transmission head comprises a first electrically conductive plate insulated from the patient by at least an air gap and the reception head comprises a second electrically conductive plate insulated from the patient by at least an air gap, and an RF field is set up between the first and second electrically conductive plates for heating the RF absorption enhancers.

66. The method according to any of claims 1, 44, 46, 47, 48, 49, 50, 62, and 63 wherein the heating of the RF absorption enhancers is caused without a separate, external magnetic field to induce heating of the RF absorption enhancers by the RF signal, and further wherein the transmission head comprises a first electrically conductive plate insulated from the patient by at least an air gap and the reception head comprises a second electrically conductive plate insulated from the patient by at least an air gap, and an RF field is set up between the first and second electrically conductive plates for heating the RF absorption enhancers.

67. The method according to any of claims 1-10, 22-24, 44, 46-50, 62 and 63, wherein the RF signal comprises a signal having a frequency component at one of about 13.56 MHz and about 27.12 MHz for heating the RF absorption enhancers.

68. The method according to any of claims 1-10, 22-24, 44, 46-50, 62 and 63, wherein the RF signal is a frequency modulated (FM) RF signal having parameters selected to correspond to specific RF absorbing particles being used in the RF absorption enhancers.

69. The method according to claim 68 wherein the RF signal is a frequency modulated (FM) RF signal having a center frequency corresponding to a resonant frequency of a nominal RF absorbing particle being used in the RF absorption enhancers and the modulation of the FM RF signal corresponds to a range of a parameter of the RF absorbing particles being used in the RF absorption enhancers.

70. The method according to any of claims 1-10, 22-24, 44, 46-50, 62 and 63, wherein RF absorbing particles of the RF absorption enhancers have an associated manufacturing tolerance resulting in an associated range of resonant frequencies and further wherein the RF signal comprises a plurality of frequencies corresponding to the range of resonant frequencies associated with the manufacturing tolerance of the RF absorbing particles of the RF absorption enhancers.

71. The method according to any of claims 1-10, 22-24, 44, 46-50, 62 and 63, wherein the transmission head comprises a first electrically conductive plate insulated from the patient by at least an air gap and the reception head comprises a second electrically conductive plate insulated from the patient by at least an air gap, and an RF field is set up between the first and second electrically conductive plates for heating the RF absorption enhancers, and further wherein the RF signal comprises a signal having a frequency component at one of about 13.56 MHz and about 27.12 MHz for heating the RF absorption enhancers.

72. The method according to any of claims 1, 44, 46, 47, 48, 49, 50, 62, and 63 wherein the heating of the RF absorption enhancers is caused without a separate, external magnetic field to induce heating of the RF absorption enhancers by the RF signal, further wherein the transmission head comprises a first electrically conductive plate insulated from the patient by at least an air gap and the reception head comprises a second electrically conductive plate insulated from the patient by at least an air gap, and an RF field is set up between the first and second electrically conductive plates for heating the RF absorption enhancers, and further wherein the RF signal comprises a signal having a frequency component at one of about 13.56 MHz and about 27.12 MHz for heating the RF absorption enhancers.

73. The method according to any of claims 1, 44, 46, 47, 48, 49, 50, 62, and 63 wherein the wherein the step of introducing the RF absorption enhancers into the patient comprises injecting the RF absorption enhancers into the patient.

* * * * *

UNITED STATES PATENT AND TRADEMARK OFFICE
CERTIFICATE OF CORRECTION

| | | |
|---|---|---|
| PATENT NO. | : 7,510,555 B2 | Page 1 of 1 |
| APPLICATION NO. | : 11/050422 | |
| DATED | : March 3, 2009 | |
| INVENTOR(S) | : John Kanzius | |

It is certified that error appears in the above-identified patent and that said Letters Patent is hereby corrected as shown below:

On the title page,

[*] Notice:   Subject to any disclaimer, the term of this patent is extended or adjusted under 35 USC 154(b) by 267 days Delete the phrase "by 267 days" and insert -- by 648 days --

Signed and Sealed this

Twentieth Day of April, 2010

David J. Kappos
*Director of the United States Patent and Trademark Office*